United States Patent [19]
Fujii et al.

[11] Patent Number: 5,141,490
[45] Date of Patent: Aug. 25, 1992

[54] SINGLE-NEEDLE TYPE PLASMA SEPARATION APPARATUS AND PLASMA COLLECTION APPARATUS

[75] Inventors: Tatsuya Fujii; Hiroyuki Keino, both of Kanagawa, Japan

[73] Assignee: Terumo Kabushiki Kaisha, Tokyo, Japan

[21] Appl. No.: 515,730

[22] Filed: Apr. 26, 1990

[30] Foreign Application Priority Data

Jun. 25, 1989 [JP] Japan .................................. 1-163339

[51] Int. Cl.⁵ ............................................ A61M 37/00
[52] U.S. Cl. .................................... 604/6; 210/195.2; 210/257.2; 210/651; 604/4
[58] Field of Search ........................................ 604/4–6; 210/195.2, 257.2, 651

[56] References Cited

U.S. PATENT DOCUMENTS

| | | | |
|---|---|---|---|
| 4,322,298 | 3/1982 | Persidsky | 604/6 X |
| 4,639,243 | 1/1987 | Schmidt et al. | 604/6 |
| 4,655,742 | 4/1987 | Vantard | 604/6 |
| 4,886,487 | 12/1989 | Solem et al. | 604/6 |
| 4,894,164 | 1/1990 | Polaschegg | 604/5 X |
| 4,904,234 | 2/1990 | Shimomura et al. | 604/5 |
| 4,923,449 | 5/1990 | Toya et al. | |
| 4,966,709 | 10/1990 | Nose et al. | 604/6 X |

FOREIGN PATENT DOCUMENTS

| | | |
|---|---|---|
| 63-23644 | 1/1988 | Japan . |
| 63-235866 | 9/1988 | Japan . |
| WO88/0264 | 4/1988 | World Int. Prop. O. . |

*Primary Examiner*—Mickey Yu
*Assistant Examiner*—Kerry Owens
*Attorney, Agent, or Firm*—Frishauf, Holtz, Goodman & Woodward

[57] ABSTRACT

The single-needle type plasma separation apparatus of the present invention comprises a blood collection needle; a blood collection container; a first blood transportation tube connecting the blood collection needle to the blood collection container; a blood separator; a second blood transportation tube connecting the blood collection container to a blood inlet of the blood separator; a third blood transportation tube connecting a blood outlet of the blood separator to the first blood transportation tube; a plasma collection container; a plasma transportation tube connecting a plasma outlet of the plasma separator to the plasma collection container; and a blood collection container receptacle including a receiving portion for the blood collection container and capable of pressurizing and depressurizing the interior of the receiving portion. Because the single-needle type plasma separation apparatus of the present invention is provided with the blood collection container receptacle including the receiving portion for the blood collection container and capable of pressurizing and depressurizing the interior of the receiving portion, it is possible to carry out the collection of blood into the blood collection container, the transportation of the collected blood to the plasma separator, and the return of the concentrated red blood cells from the plasma separator. Therefore, the present invention affords the advantages that the circuit construction is simple, the whole size of the apparatus is small, the apparatus can be used even in a narrow car for blood donation because there is no necessity for ensuring a head for circulating blood through a plasma separator, parts to be handled can be gathered, improving the operability, and plasma can easily be collected. Furthermore, the blood transportation tubes connecting the components to one another can be shortened, the volume for priming of the plasma separation apparatus can be made small, and an automation of the operation becomes possible.

21 Claims, 23 Drawing Sheets

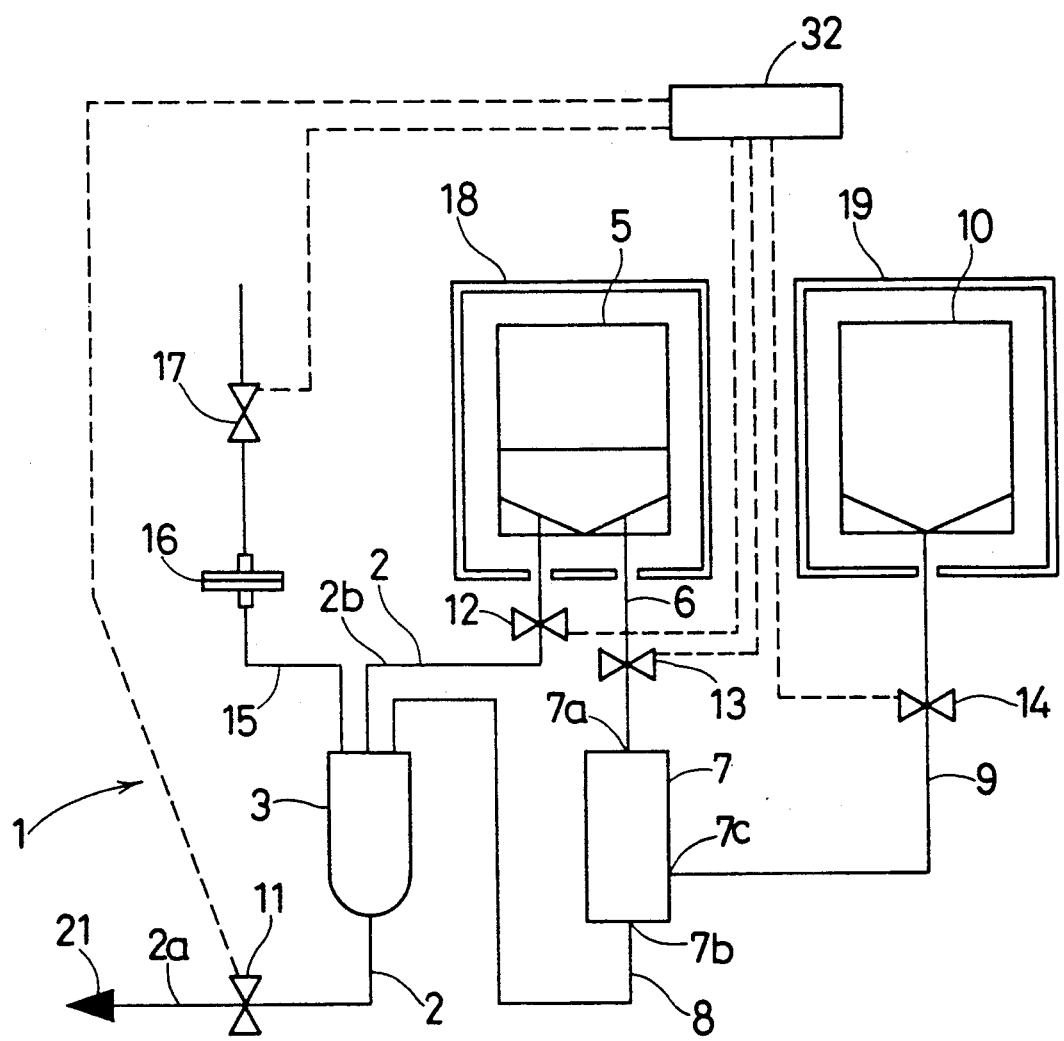

SET PRESSURE 0.8~0.9 OF
SET PRESSURE

TIME

PUMP

ON
OFF

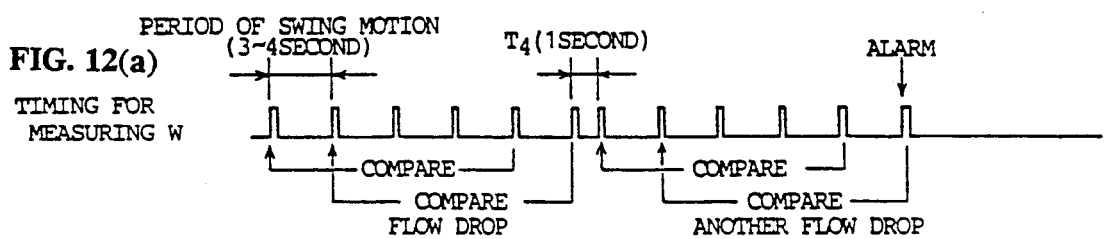
FIG. 12(a) TIMING FOR MEASURING W
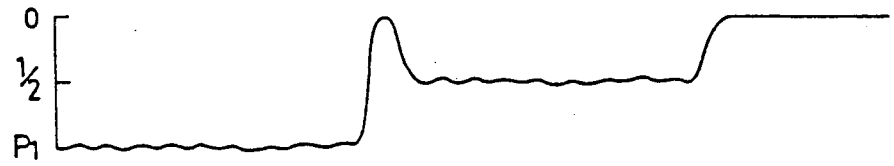
FIG. 12(b) BLOOD COLLECTION PRESSURE
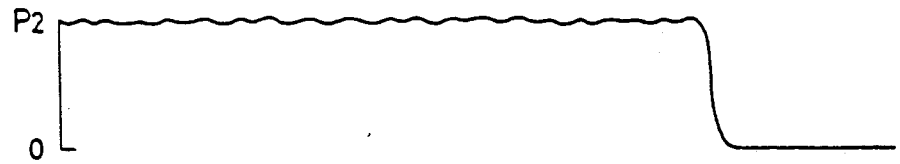
FIG. 12(c) CUFF PRESSURE
FIG. 12(d) LEAK VALVE 5,141,490

SINGLE-NEEDLE TYPE PLASMA SEPARATION APPARATUS AND PLASMA COLLECTION APPARATUS

BACKGROUND OF THE INVENTION

This invention relates to a plasma separation apparatus for use in collecting plasma from blood, more particularly, to a single-needle type plasma separation apparatus and a plasma collection apparatus for collecting plasma by using a single-needle type plasma separation circuit.

As a conventional plasma separation apparatus, there has been proposed a double-needle type plasma separation apparatus in which plasma separation is continuously carried out by utilizing gravity by the manner that two blood collection containers are lifted up and down alternatively, for example, as shown in FIG. 14 (Japanese Patent Kokai JP-A-59-209347).

There has also been proposed a single-needle type plasma separation apparatus in which plasma separation is intermittently carried out by utilizing gravity by the manner that a single blood collection container is lifted up and down, for example, as shown in FIG. 15 (Japanese Patent Kokai JP-A-60-7852).

Referring to FIG. 14, in the double-needle type plasma separation apparatus in which plasma separation is continuously carried out by utilizing gravity by the manner that the blood collection containers 65 and 66 are lifted up and down alternatively, a donor need be stabbed with two puncture needles, that is, a blood collection needle 61 and a blood return needle 68. Further in this apparatus, blood collected from a vein of the donor must be circulated with a head between the donor and a plasma separator 63. Then a plasma collection container 60 and one of the concentrated red blood cell reservoirs 65 and 66 must be kept below the plasma separator 63 during plasma collection operation. Thus, it is difficult to carry out the plasma collection operation because it must be done at a low posture. Besides, it is also difficult to ensure the necessary head between the donor and plasma separator 63 in a narrow place, particularly within a car for blood donation. Further, in this conventional plasma separation apparatus, their components which need be handled are relatively apart from one another, resulting bad operability.

Referring to FIG. 15, also in the single-needle type plasma separation apparatus in which plasma separation is intermittently carried out by utilizing gravity by the manner that the blood collection container 75 is lifted up and down, blood collected from a vein of a donor must be circulated with a head between the donor and a plasma separator 73. Then a plasma collection container 79 and the concentrated red blood cell reservoir 75 must be kept below the plasma separator 73 during plasma collection operation. Thus, it is difficult to carry out the plasma collection operation because it must be done at a low posture. Besides, it is also difficult to ensure the necessary head between the donor and plasma separator 73 in a narrow place, particularly within a car for blood donation. Further, also in this conventional plasma separation apparatus, their components which need be handled are relatively apart from one another, resulting bad operability.

SUMMARY OF THE INVENTION

Accordingly, it is an object of the present invention to provide a single-needle type plasma separation apparatus and a plasma collection apparatus for collecting plasma by using a single-needle type plasma separation circuit, wherein the circuit construction is simple, the whole size of the apparatus is small, the apparatus can be used even in a narrow car for blood donation, there is no necessity for ensuring a head for circulating blood through a plasma separator, parts to be handled can be gathered, and plasma can easily be collected.

The above object is attained by a single-needle type plasma separation apparatus comprising a blood collection needle; a blood collection container; a first blood transportation tube connecting the blood collection needle to the blood collection container; a blood separator; a second blood transportation tube connecting the blood collection container to a blood inlet of the blood separator; a third blood transportation tube connecting a blood outlet of the blood separator to the first blood transportation tube; a plasma collection container; a plasma transportation tube connecting a plasma outlet of the plasma separator to the plasma collection container; and a blood collection container receptacle including a receiving portion for the blood collection container and capable of pressurizing and depressurizing the interior of the receiving portion.

The above object is also attained by a plasma collection apparatus to which is connected a blood separation circuit comprising a blood collection needle; a blood collection container; a first blood transportation tube connecting the blood collection needle to the blood collection container; a blood separator; a second blood transportation tube connecting the blood collection container to a blood inlet of the blood separator; a third blood transportation tube connecting a blood outlet of the blood separator to the first blood transportation tube; a plasma collection container; and a plasma transportation tube connecting a plasma outlet of the plasma separator to the plasma collection container, comprising a blood collection container receiving portion; pressurizing and depressurizing means for pressurizing or depressurizing the interior of the blood collection container receiving portion; a plasma separator attachement portion for detachably attaching the plasma separator; first shut-off means for closing the first blood transportation tube of the blood separation circuit; second shut-off means for closing the second or third blood transportation tube thereof; and third shut-off means for closing the plasma transportation tube thereof.

BRIEF DESCRIPTION OF THE DRAWINGS

FIGS. 2 and 3 are schematic illustrations of other embodiments of the single-needle type plasma separation apparatus of the present invention;

FIGS. 12(a) through 12(d) are graph representations for illustrating the operation of the plasma collection apparatus when detecting a drop of the flow rate of collected blood upon blood collection using the plasma collection apparatus of the present invention;

DETAILED DESCRIPTION OF THE PREFERRED EMBODIMENT

Figure 1:
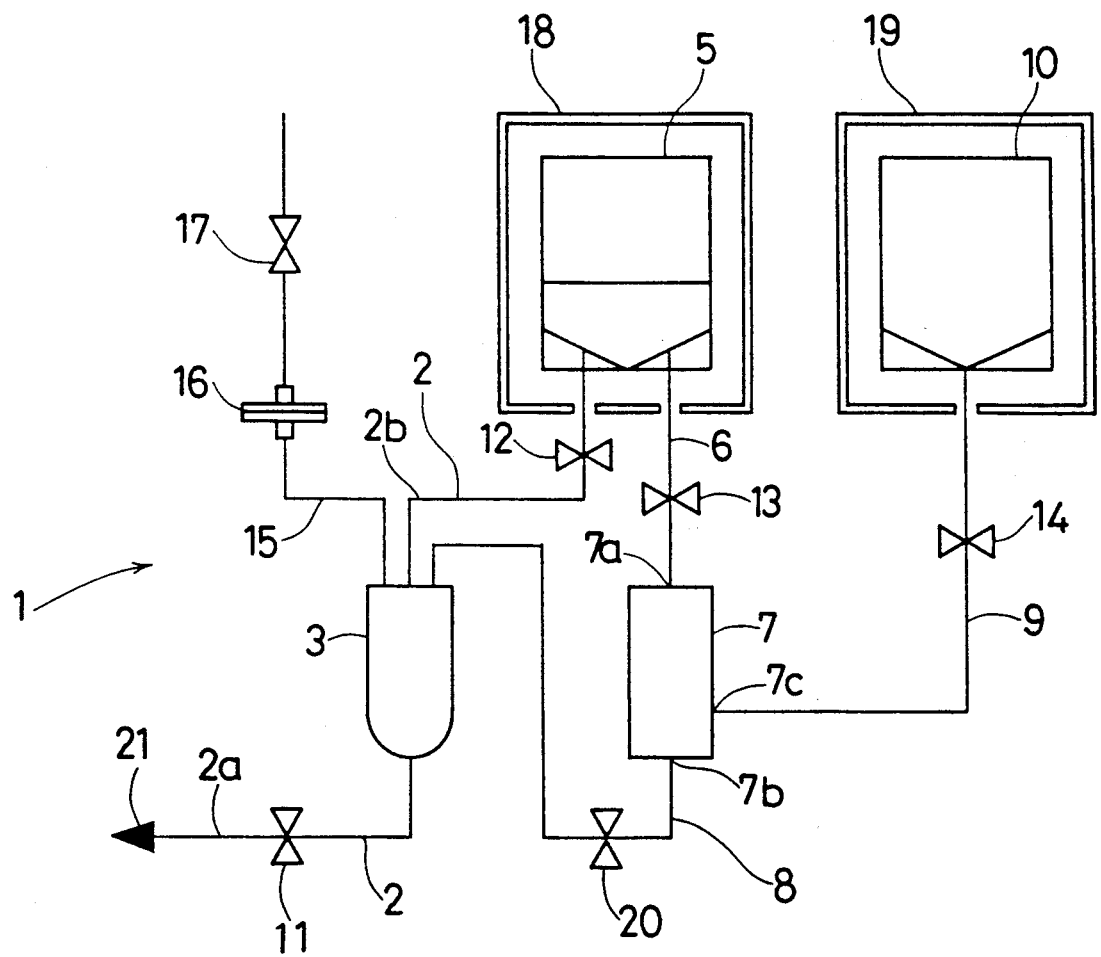
FIG. 1 is a schematic illustration of one embodiment of the single-needle type plasma separation apparatus of the present invention.

The single-needle type plasma separation apparatus of the present invention will be described with reference to embodiments shown in the drawings.

The single-needle type plasma separation apparatus 1 of the present invention comprises a blood collection needle 21; a blood collection container 5; a first blood transportation tube 2 connecting the blood collection needle 21 to the blood collection container 5; a blood separator 7; a second blood transportation tube 6 connecting the blood collection container 5 to a blood inlet 7a of the blood separator 7; a third blood transportation tube 8 connecting a blood outlet 7b of the blood separator 7 to the first blood transportation tube 2; a plasma collection container 10; a plasma transportation tube 9 connecting a plasma outlet 7c of the plasma separator 7 to the plasma collection container 10; and a blood collection container receptacle 18 including a receiving portion for the blood collection container and capable of pressurizing and depressurizing the interior of the receiving portion.

The single-needle type plasma separation apparatus of the present invention is provided with the blood collection container receptacle including the receiving portion for the blood collection container and capable of pressurizing and depressurizing the interior of the receiving portion. Thereby, it is possible to carry out the collection of blood into the blood collection container, the transportation of the collected blood to the plasma separator, and the return of the concentrated red blood cells from the plasma separator. Therefore, the present invention affords the advantages that the circuit construction is simple, the whole size of the apparatus is small, the apparatus can be used even in a narrow car for blood donation, there is no necessity for ensuring a head for circulating blood through a plasma separator, parts to be handled can be gathered, and plasma can easily be collected.

The plasma separation apparatus of the present invention will be described with reference to the embodiment shown in FIG. 1.

In the plasma separation apparatus 1 of the present invention, a well-known blood collection needle 21 made of metal or resin is used.

The first blood transportation tube 2 is connected to the blood collection needle 21 at its one end. The other end of the first blood transporation tube 2 is in fluid communication with a blood collection container 5. Alternatively, more than two blood collection containers may be connected to the other end of the first blood transporation tube 2. A blood chamber 3 is preferably disposed in the middle of the first blood transportation tube 2 as shown in FIG. 1. In this case, the first blood transportation tube 2 is divided into two first blood transportation tubes 2a and 2b and the blood chamber 3 is arranged therebetween. The blood chamber 3 is preferably provided with a communicating tube 15 for communicating the interior of the blood chamber 3 with the atmosphere, an air filter 16 and a releasing means 17. By this arrangement, it becomes possible to transport blood remaining in the first blood transportation tube 2b to the blood collection container 5, utilizing blood effectively. The blood chamber 3 may be made of a flexible or hard material having a small blood storage space. The air filter 16 is provided therein with a filter through which bacilli cannot pass but gas can. More safely, the filter does not allow blood to pass therethrough. The releasing means 17 may comprise a valve such as a two-way valve and an electromagnetic valve, or a forceps.

The second blood transportation tube 6 is in fluid communication with the blood collection container 5 at its one end. The other end of the second blood transportation tube 6 is in fluid communication with a blood inlet 7a of a plasma separator 7. The third blood transportation tube 8 is in fluid communication with a blood outlet 7b of the plasma separator 7 at its one end. The other end of the third blood transportation tube 8 is in fluid communication with the first blood transportation tube 2. In the case of the first blood transportation tube 2 having the blood chamber 3 as described above, the third blood transportation tube 8 is preferably in fluid communication with the blood chamber 3.

The plasma transportation tube 9 is in fluid communication with a plasma outlet 7c of the plasma separator 7 at its one end. The other end of the plasma transportation tube 9 is in fluid communication with a plasma collection container 10.

In the first blood transportation tube 2, shut-off means 11 and 12 are disposed at positions between the blood collection needle 21 and blood chamber 3 and between the blood chamber 3 and blood collection container 5, that is, in the first blood transportation tubes 2a and 2b, respectively. Shut-off means 13 is disposed in the second blood transportation tube 6. Shut-off means 20 is disposed in the third blood transportation tube 8. It should be noted that one of the shut-off means 13 and 20 may not be disposed. In the case that only one of them is disposed, it is preferably the shut-off means 13. Most preferably, however, both are disposed. In the plasma transportation tube 9, shut-off means 14 is disposed.

The first, second and third transportation tubes 2, 6 and 8 and plasma transportation tube 9 are preferably transparent flexible synthetic resin tubes made of, for example, flexible vinyl chloride resin or silicone rubber. The first, second and third transportation tubes 2, 6 and 8 may have the minimum lengths enough to connect the plasma separator 7 and blood collection container 5 with each other, respectively, because there is no necessity for ensuring a head therebetween. Thus, the entire length of the circuit can be short, the whole size of the apparatus can be small, and the whole construction of the apparatus can be simplified.

The blood collection container 5 and plasma collection container 10 are preferably closed-type blood reservoirs made of flexible synthetic resin, for example, flexible vinyl chloride resin. Alternatively, they are open-type blood reservoirs made of rigid synthetic resin, for example, polycarbonate or rigid vinyl chloride resin having hydrophobic filters not allowing bacilli to pass. Further, in the blood collection container 5, there is contained an anticoagulant liquid such as ACD liquid, CPD liquid, sodium citrate, and heparin. The anticoagulant liquid is preferably a physiological isotonic liquid. This is because the concentrated red blood cells which were collected in the blood collection container 5 from a donor and from which plasma has been separated is directly returned to the donor. By disposing the physiological isotonic anticoagulant liquid in the blood collection container 5 in advance, an anticoagulant injection line can be omitted, making the plasma separation apparatus more small. Further, in the plasma separation apparatus 1 of the present invention, since the second blood transportation tube 6 connecting the blood collection container 5 to the plasma separator 7 is not in fluid communication with the first blood transportation tube 2, blood does not enter the second blood transportation tube 6 upon blood collection. Therefore, there is no necessity of removal of blood from the second blood transportation tube 6 and no possibility of blood clotting therein.

The plasma separator 7 has a blood inlet 7a, a blood outlet 7b for concentrated red blood cells, a blood separation function for separating plasma from blood cells, and a plasma outlet 7c. The construction of the plasma separator may be hollow fiber membrane type or flat membrane type.

The blood collection container receptacle 18 has a receiving portion for the blood collection container 5 and a function of pressurizing and depressurizing the interior of the receiving portion. The receiving portion has a volume capable of receiving the blood collection container when containing the maximum amount of blood in the case of the blood collection container 5 being flexible. The interior of the receiving portion is depressurized to transport blood into the blood collection container through the first blood transportation tube 2. The interior of the receiving portion is pressurized to transport blood into the plasma separator 7 from the blood collection container and return concentrated red blood cells to the donor from the plasma separator 7 through the third and first blood transportation tubes 8 and 2 and blood collection needle 21. More specifically, suitable is the blood collection container receptacle 18 including a receiving portion capable of being closed in the state of receiving the blood collection container, and a pump for suction and feed which is connected to the receiving portion as disclosed in the Japanese Patent Publication JP-B-51-3153 or Japanese Patent Kokai JP-A-63-23644. More preferably is the blood collection container receptacle 18 provided with a stirring function for blood in the blood collection container as disclosed in the Japanese Patent Publication JP-B-51-3153 or Japanese Patent Kokai JP-A-63-23644. The stirring function is for stirring the anticoagulant liquid and blood in the blood collection container 5. The stirring function can be carried out by, for example, repeating up and down movements of both front and rear end portions of the blood collection container receiving portion as disclosed in the Japanese Patent Publication JP-B-51-3153. Alternatively, the whole of the receiving portion is vibrated.

The embodiment shown in FIG. 1 includes a plasma collection container receptacle 19. The plasma collection container receptacle 19 has a receiving portion for the plasma collection container 10 and a function of depressurizing the interior of the receiving portion. The receiving portion has a volume capable of receiving the plasma collection container when containing the maximum amount of plasma in the case of the plasma collection container 10 being flexible. The interior of the receiving portion is depressurized to transport plasma into the plasma collection container from the plasma separator 7. The plasma collection container receptacle 19 suitably has the same construction as the blood collection container receptacle 18 described above. TMP (Trans Membrane Pressure) of the plasma separator can be varied upon plasma separation by selecting the pressure for depressurizing the plasma collection container receptacle 19. The plasma collection container receptacle 19 has no need of pressurizing and stirring functions unlike the blood collection container receptacle 18.

Figure 2:
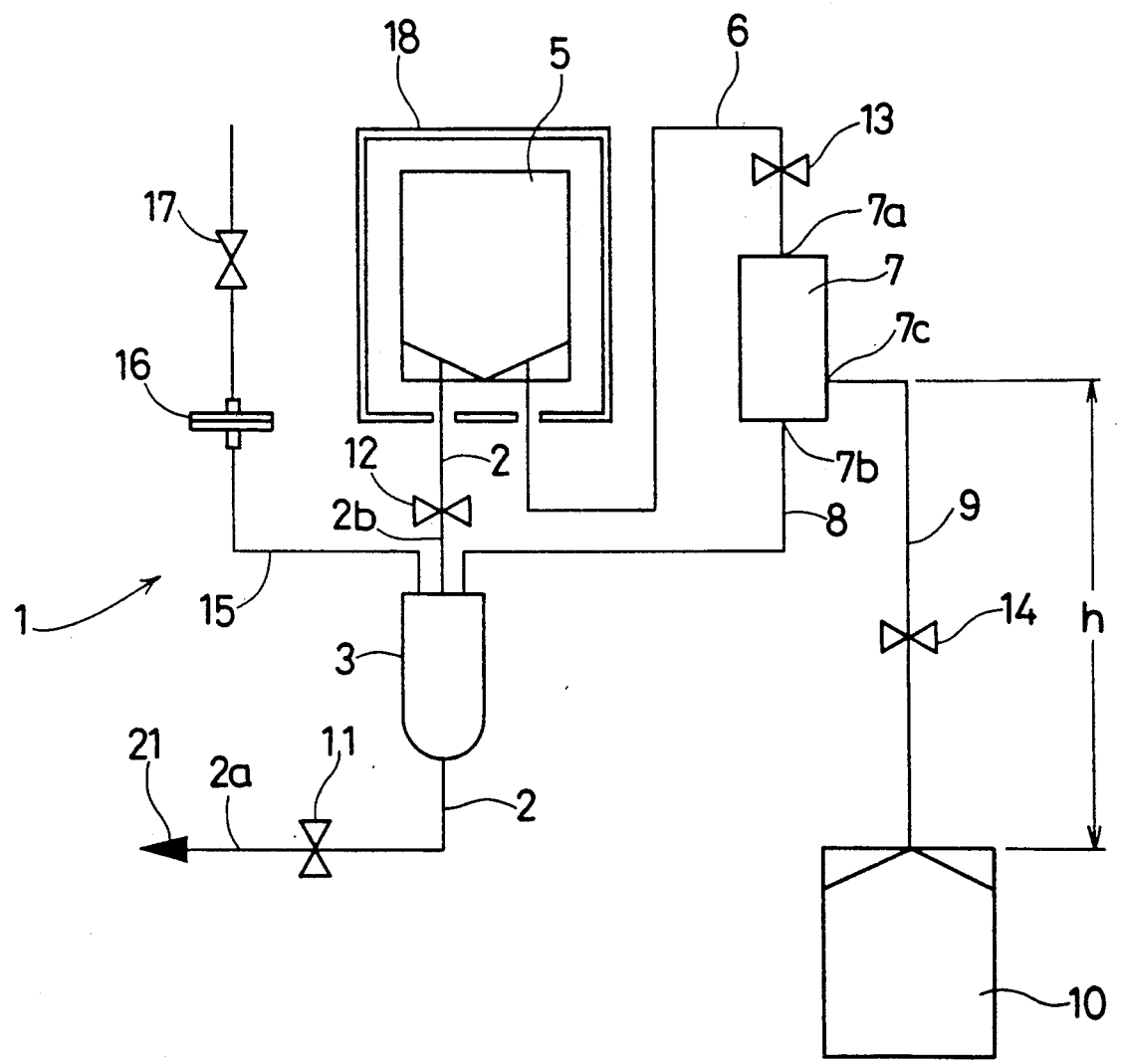

The plasma collection container receptacle 19 is not necessary. For example, the plasma transportation tube 9 can have the length and flexibility enough to change the level of the plasma collection container 10 with respect to the plasma separator 7 so that plasma is transported by a head therebetween as shown in FIG. 2. By this construction, plasma can be transported to the plasma collection container only by changing the position of the plasma collection container upon plasma separation, omitting enforcing means for transporting plasma. Further, TMP of the plasma separator can be varied upon plasma separation by selecting the position of the plasma collection container.

The plasma transportation tube 9 may be provided with enforcing means (not shown) for transporting plasma. In that case, the plasma transportation tube 9 may be provided with no shut-off means. In the case of the plasma transportation tube 9 provided with the enforcing means, the plasma collection container receptacle 19 may not be used and the position of the plasma collection container 10 relative to the plasma separator 7 may not be changed. The enforcing means preferably comprises a pump such as a roller pump and a peristaltic pump.

The shut-off means 11, 12, 13, 14 and 20 may comprise forceps or electromagnetic clamps. The shut-off means 11, 12, 13 and 14 (in the case of no shut-off means 20) and releasing means 17 may be provided with switching means 32 outputting switching signals as shown in FIG. 3. The switching means 32 is electrically connected to the above four shut-off means and releasing means 17 and is provided with a mode selection switch for selecting a mode (blood collection mode, blood transportation mode for transporting blood from the second blood transportation tube 2b, or blood return and plasma separation mode). The mode selection switch is operated to change the above four shut-off means and releasing means 17 in their opening and closing states in accordance with the aimed mode. In the blood collection mode, the shut-off means 11 and 12 are open and the shut-off means 13 and 14 and releasing means 17 are closed. Although it is preferable that the shut-off means 14 is also closed, it may be open. In the blood transportation mode for transporting blood from the second blood transportation tube 2b, the shut-off means 11 is closed and the shut-off means 12 and releasing means 17 are open. In the blood return and plasma separation mode, the shut-off means 12 and releasing means 17 are closed and the shut-off means 11, 13 and 14 are open. The first blood transportation tube may be provided with an anticoagulant liquid transportation tube and an anticoagulant liquid container connected to the anticoagulant liquid transportation tube. By this construction, times of operations of blood collection and plasma separation can be carried out with a single blood collection container.

Next, an embodiment of the plasma collection apparatus of the present invention will be described.

Figure 4A:
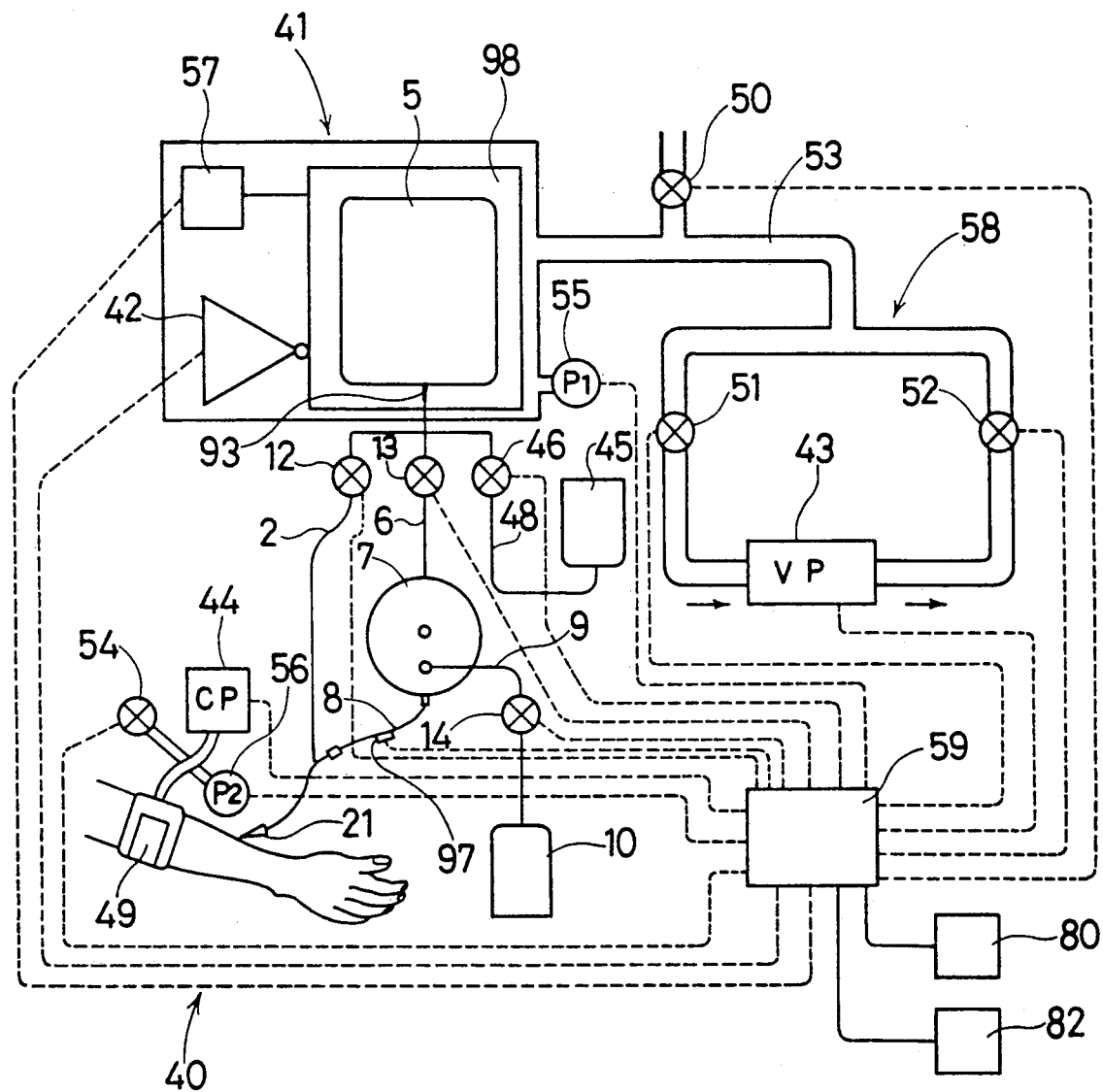
FIGS. 4(a) and 4(b) are schematic illustrations of one embodiment of the plasma collection apparatus of the present invention to which a single-needle type plasma separation circuit is connected.

A schematic illustration of the basic construction of the plasma collection apparatus 40 of this embodiment is shown in FIG. 4(a). FIG. 4(a) shows the plasma collection apparatus 40 to which a single-needle type plasma separation circuit has been connected.

The plasma collection apparatus 40 to which is connected the blood separation circuit comprising a blood collection needle 21; a blood collection container 5; a first blood transportation tube 2 connecting the blood collection needle 21 to the blood collection container 5; a blood separator 7; a second blood transportation tube 6 connecting the blood collection container 5 to a blood inlet of the blood separator 7; a third blood transportation tube 8 connecting a blood outlet of the blood separator 7 to the first blood transportation tube 2; a plasma collection container 10; and a plasma transportation tube 9 connecting a plasma outlet of the plasma separator 7 to the plasma collection container 10, comprises a blood collection container receiving portion 41; pressurizing and depressurizing means 58 for pressurizing or depressurizing the interior of the blood collection container receiving portion 41; a plasma separator attachment portion for detachably attaching the plasma separator 7; first shut-off means 12 for closing the first blood transportation tube 2 of the blood separation circuit; second shut-off means 13 for closing the second or third blood transportation tube 6 or 8 thereof; and third shut-off means 14 for closing the plasma transportation tube 9 thereof.

The plasma collection apparatus 40 further comprises swinging means 42 for shaking the blood collection container received by the blood collection container receiving portion 41; pressure detecting means 55 for detecting the internal pressure of the blood collection container receiving portion 41; weight detecting means 57 for detecting the weight of the blood collection container received by the blood collection container receiving portion; pressurizing means 44 for pressurizing a cuff 49 wound around an arm of a donor; and pressure detecting means 56 for detecting the pressure of the cuff 49.

The single-needle type plasma separation circuit in this example includes an anticoagulant liquid container 45 and an anticoagulant liquid transportation tube 48 connecting the anticoagulant liquid container 45 to the blood collection container 5. Further, the plasma collection apparatus 40 includes fourth shut-off means 46 for closing the anticoagulant liquid transportation tube 48.

Figure 4B:
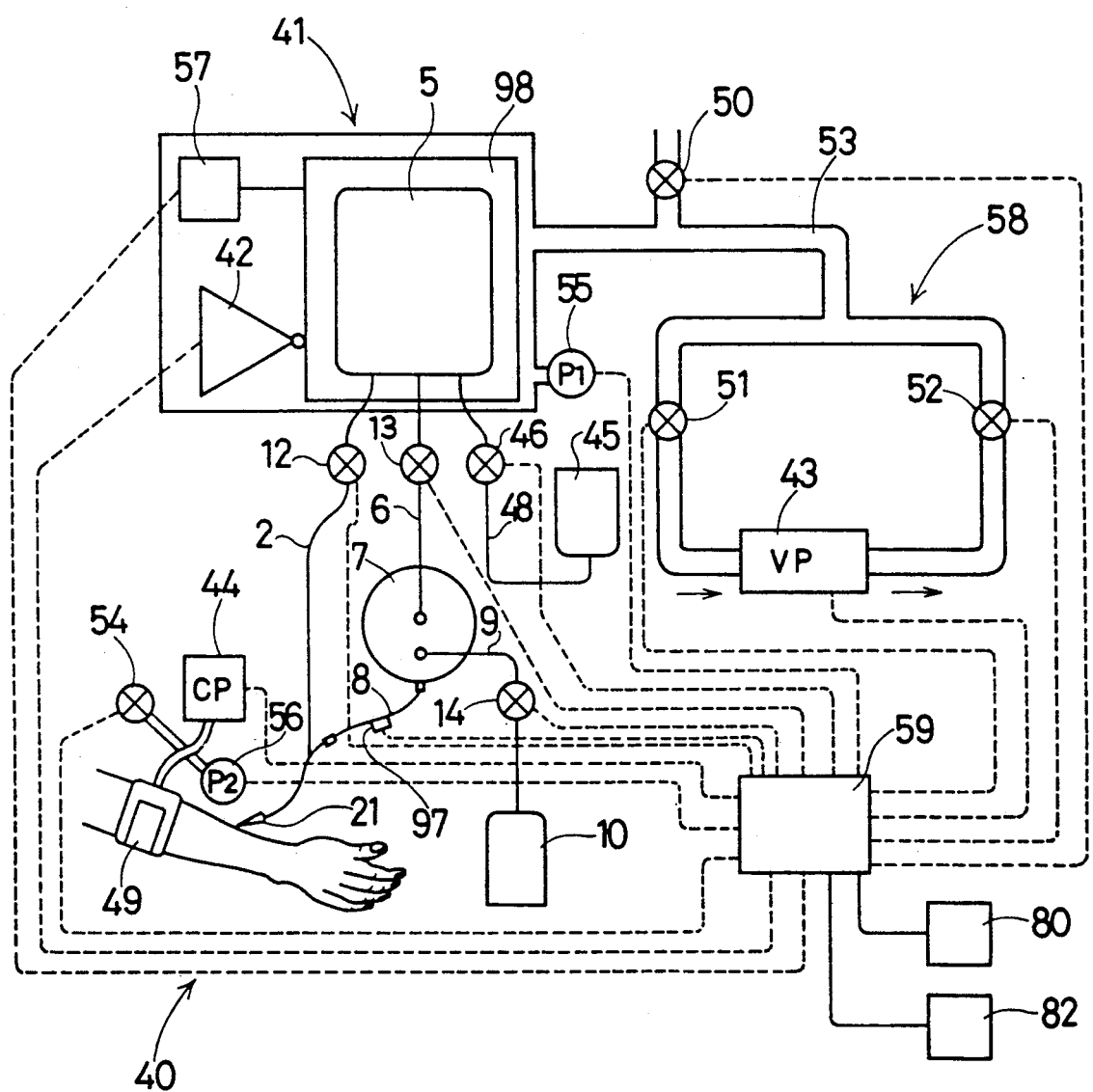
Figure 5:
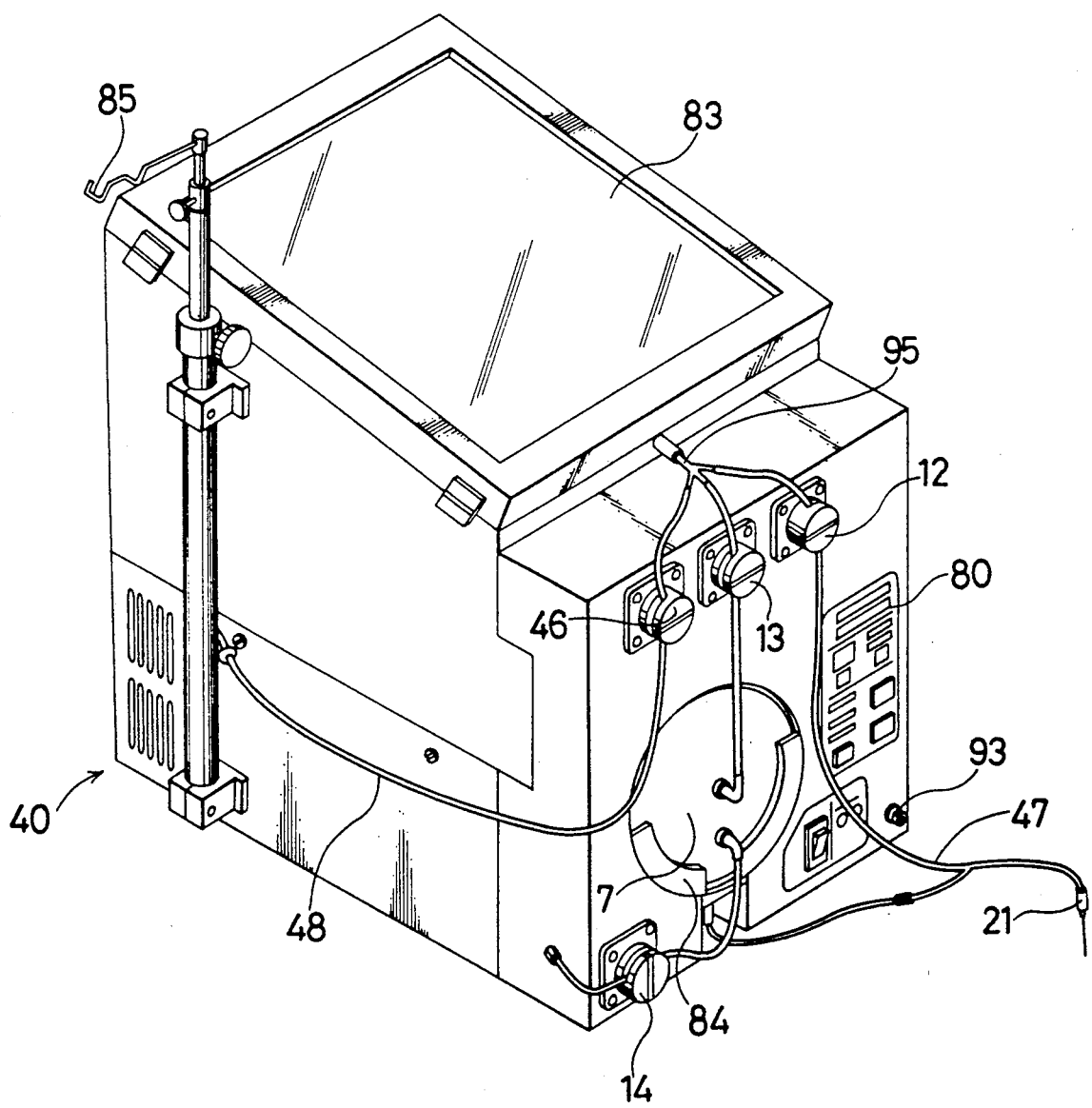
FIG. 5 is a perspective view of the embodiment of the plasma collection apparatus of the present invention to which the single-needle type plasma separation circuit is connected.

In the single-needle type plasma separation circuit, the first and second blood transportation tubes 2 and 6 and anticoagulant liquid transportation tube 48 are in fluid communication with the blood collection container 5 through a tube 93 connected to the blood collection container 5, and a branched tube 95 as shown in FIGS. 4(a) and 5. The first and second blood transportation tubes 2 and 6 and anticoagulant liquid transportation tube 48 may directly be connected to the blood collection container 5 as shown in FIG. 4(b).

More specifically, the pressurizing and depressurizing means 58 comprises a feed and exhaust circuit 53, pressurizing/depressurizing change-over valves 51 and 52, a vacuum pump 43, and a leak valve 50. The swinging means 42 comprises a swinging crank for swinging a blood collection container receiving table 98 disposed in the blood collection container receiving portion 41, and a motor. All of the pressurizing and depressurizing means 58, swinging means 42, pressure detecting means 55, weight detecting means 57, pressurizing means 44 for the cuff 49, pressure detecting means 56 for the cuff 49, leak valve 54, and shut-off means 12, 13, 14 and 46 are electrically connected to a controller 59. The controller 59 controls all of them as described later with flow charts of FIGS. 8(a) through 8(g), 9(a), 9(b) and 10.

Figure 6:
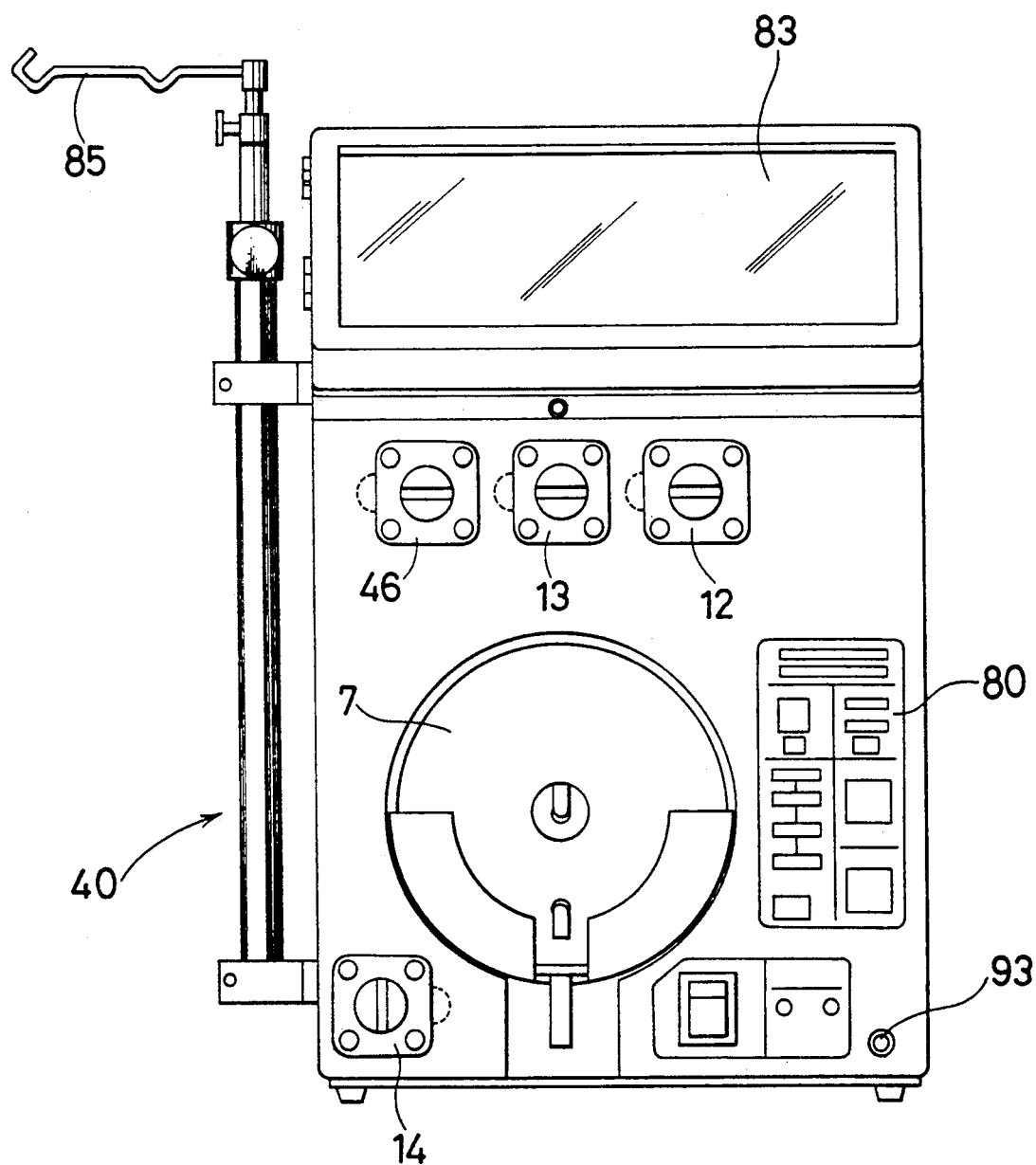
FIG. 6 is a front elevation of the embodiment of the plasma collection apparatus of the present invention to which only a plasma separator is attached.
Figure 7:
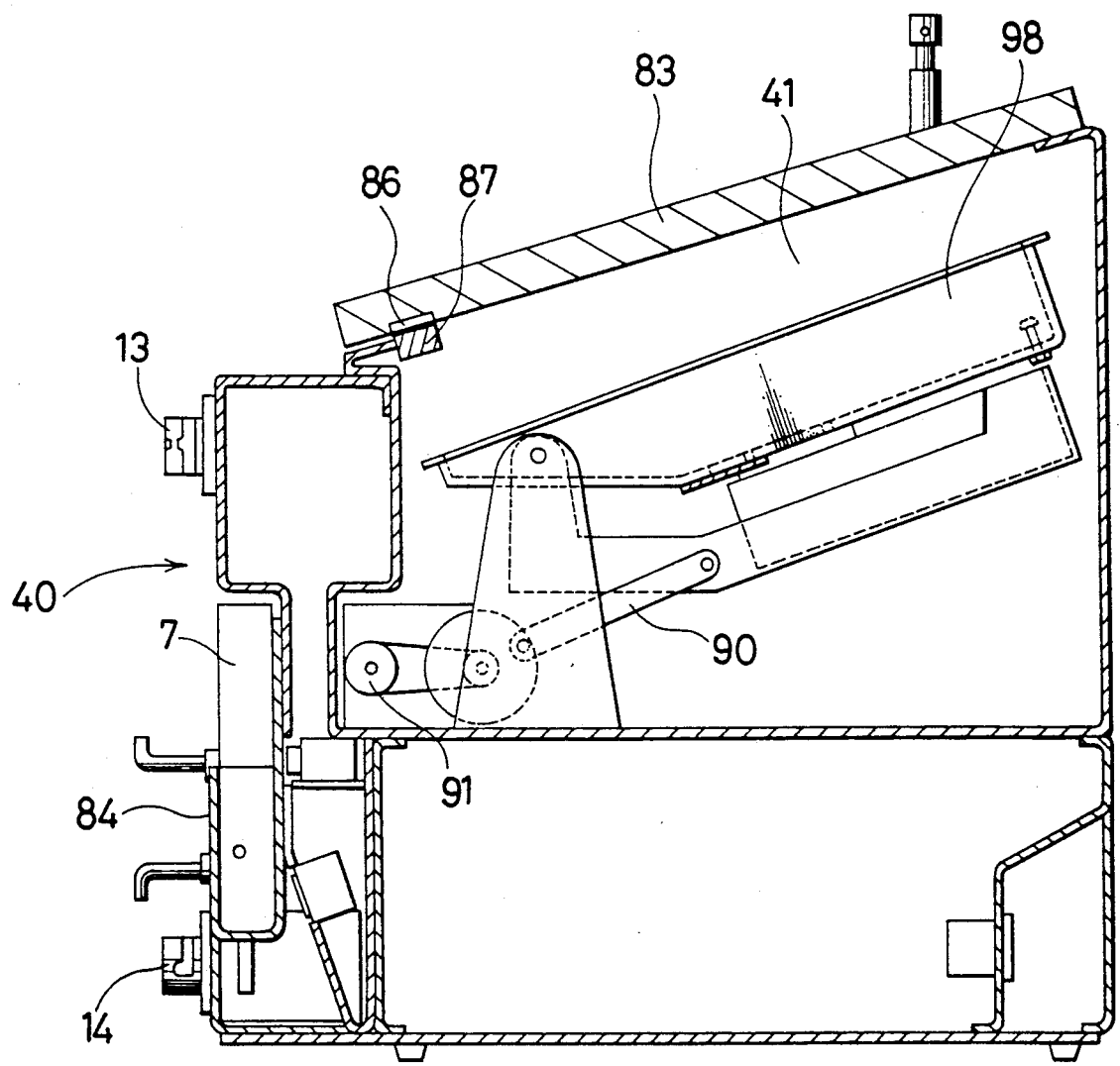
FIG. 7 is a schematic cross sectional view taken along the center line of FIG. 6.
Figure 8:
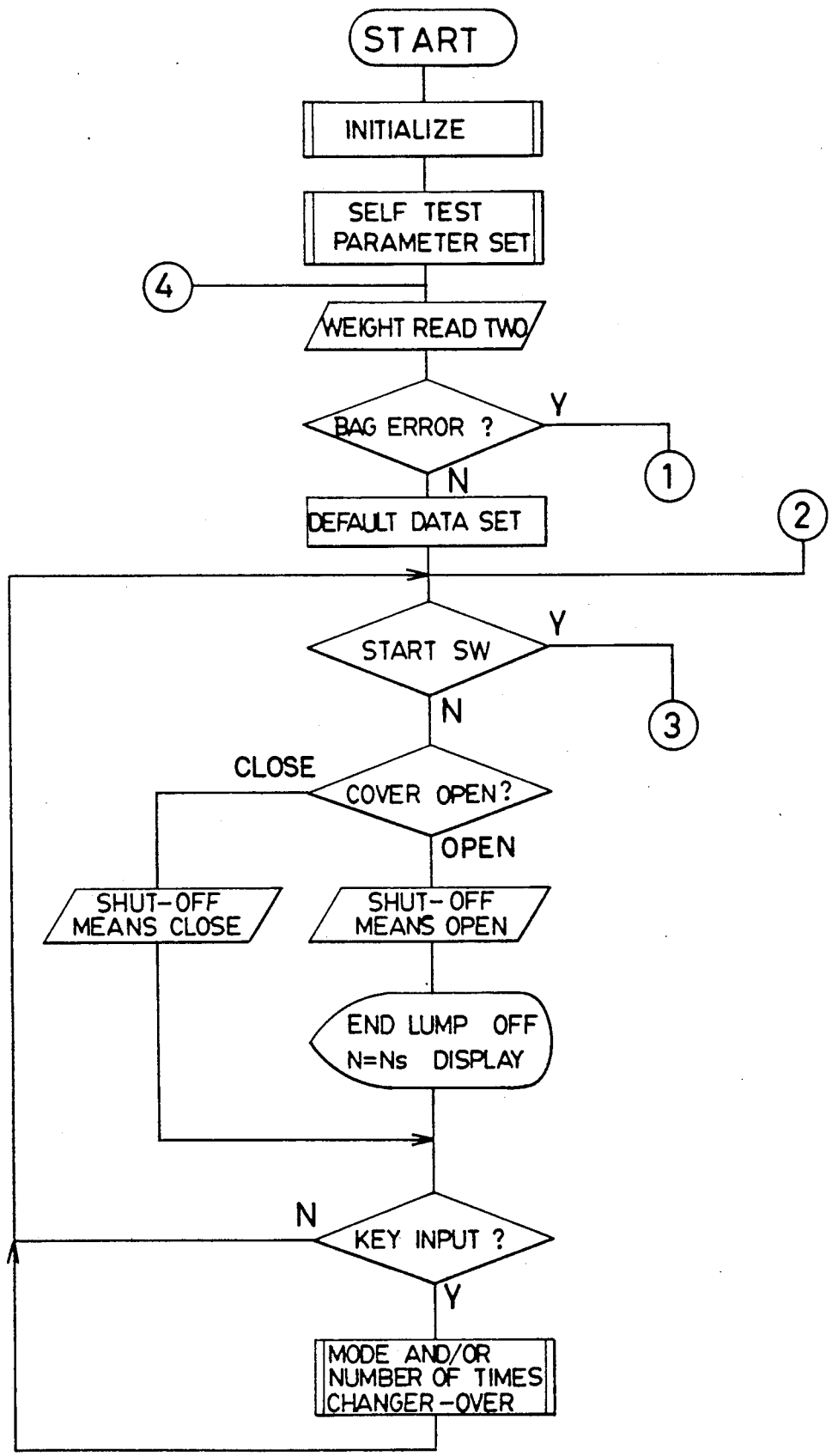
FIGS. 8(a) through 8(g) are flow charts for illustrating the operation of the embodiment of the plasma collection apparatus of the present invention.
Figure 8:
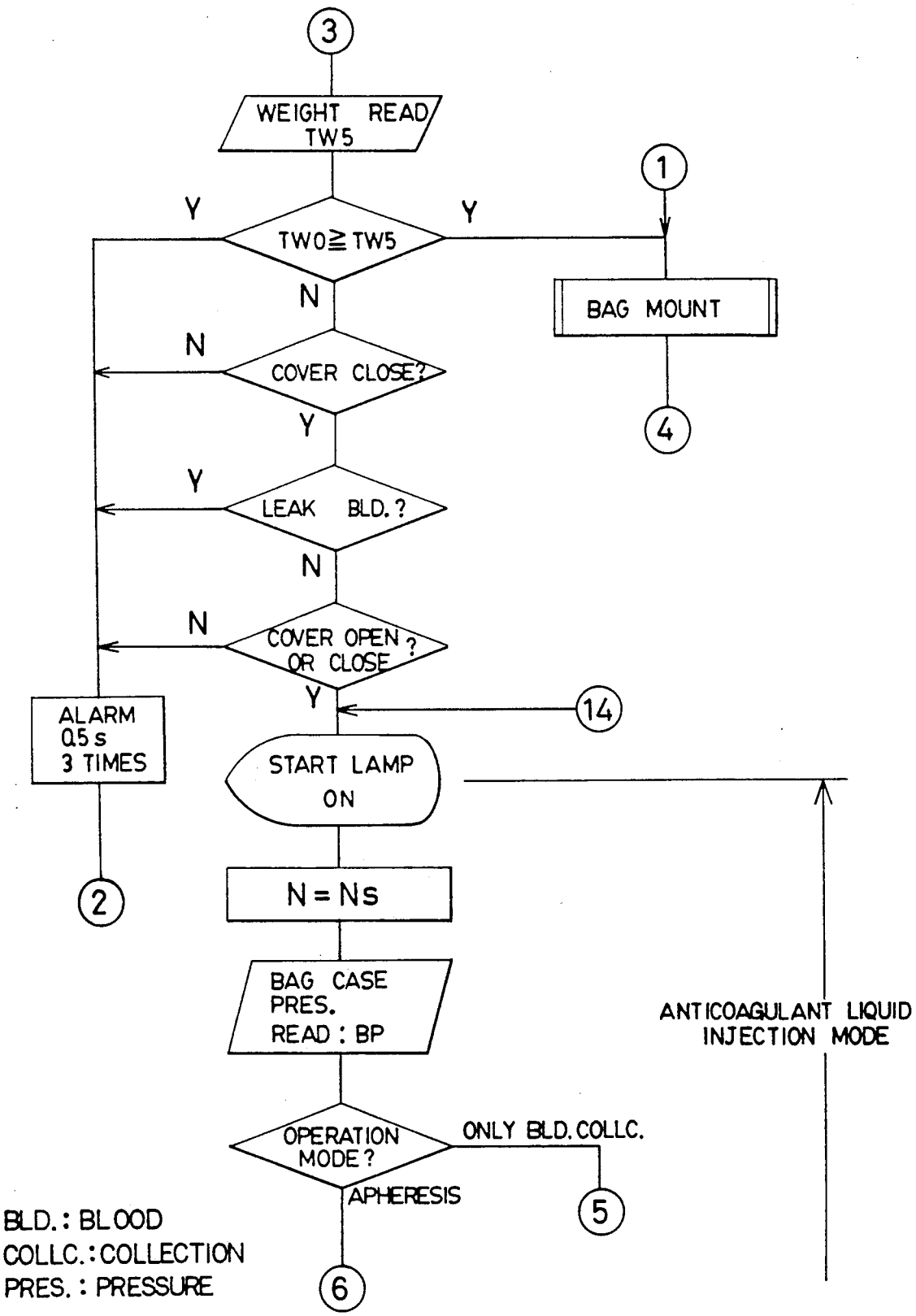
Figure 8C:
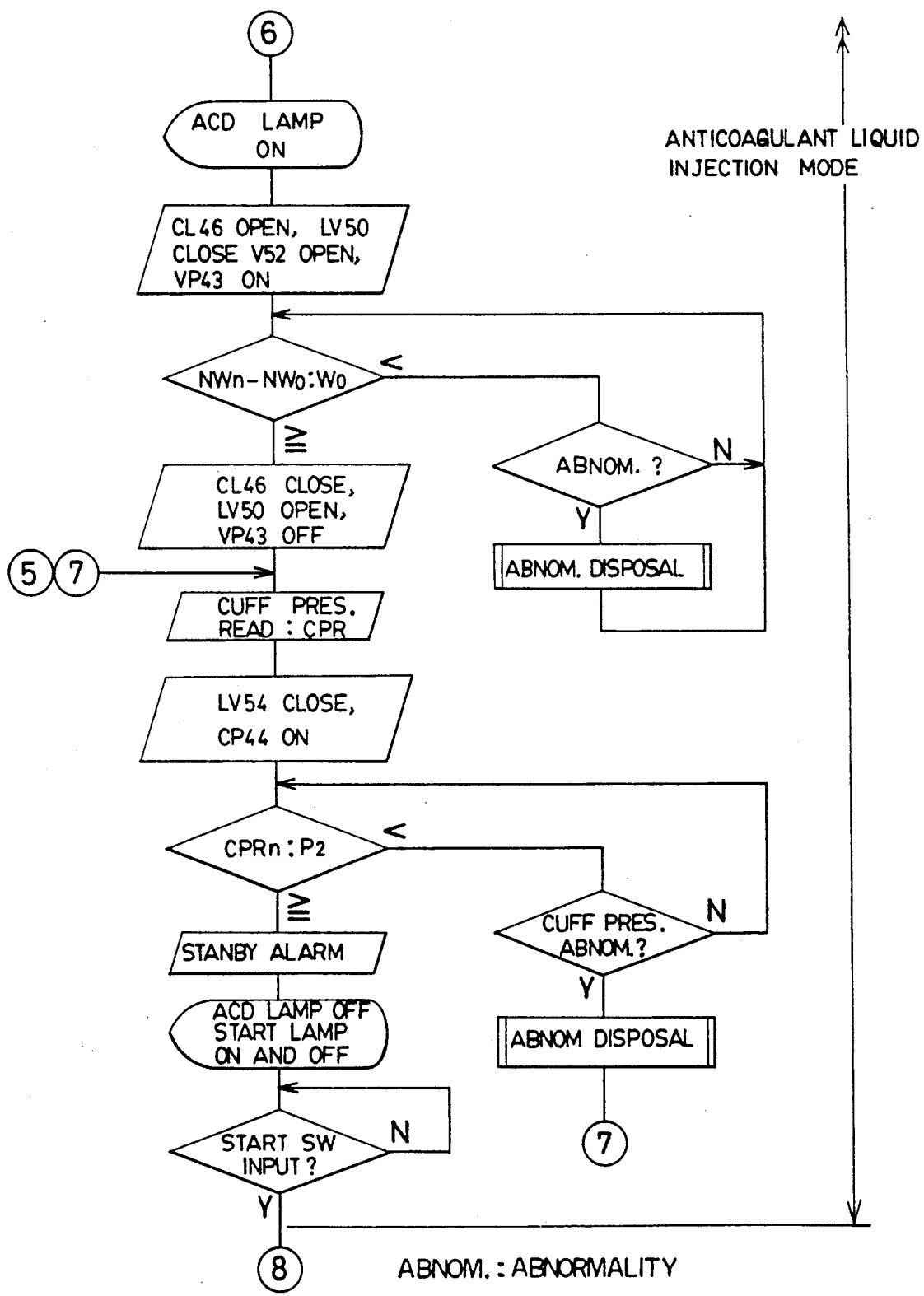
Figure 8D:
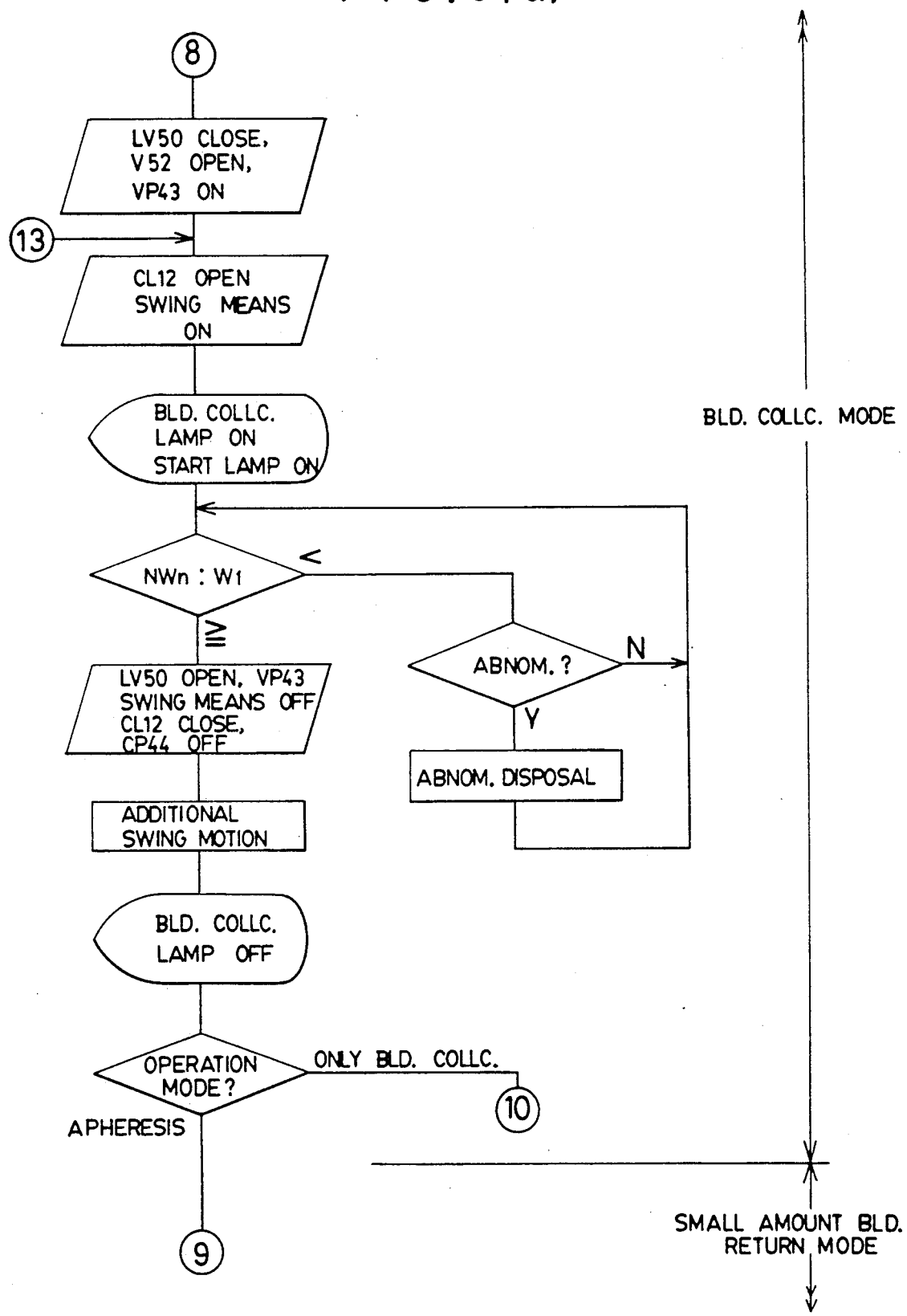
Figure 8E:
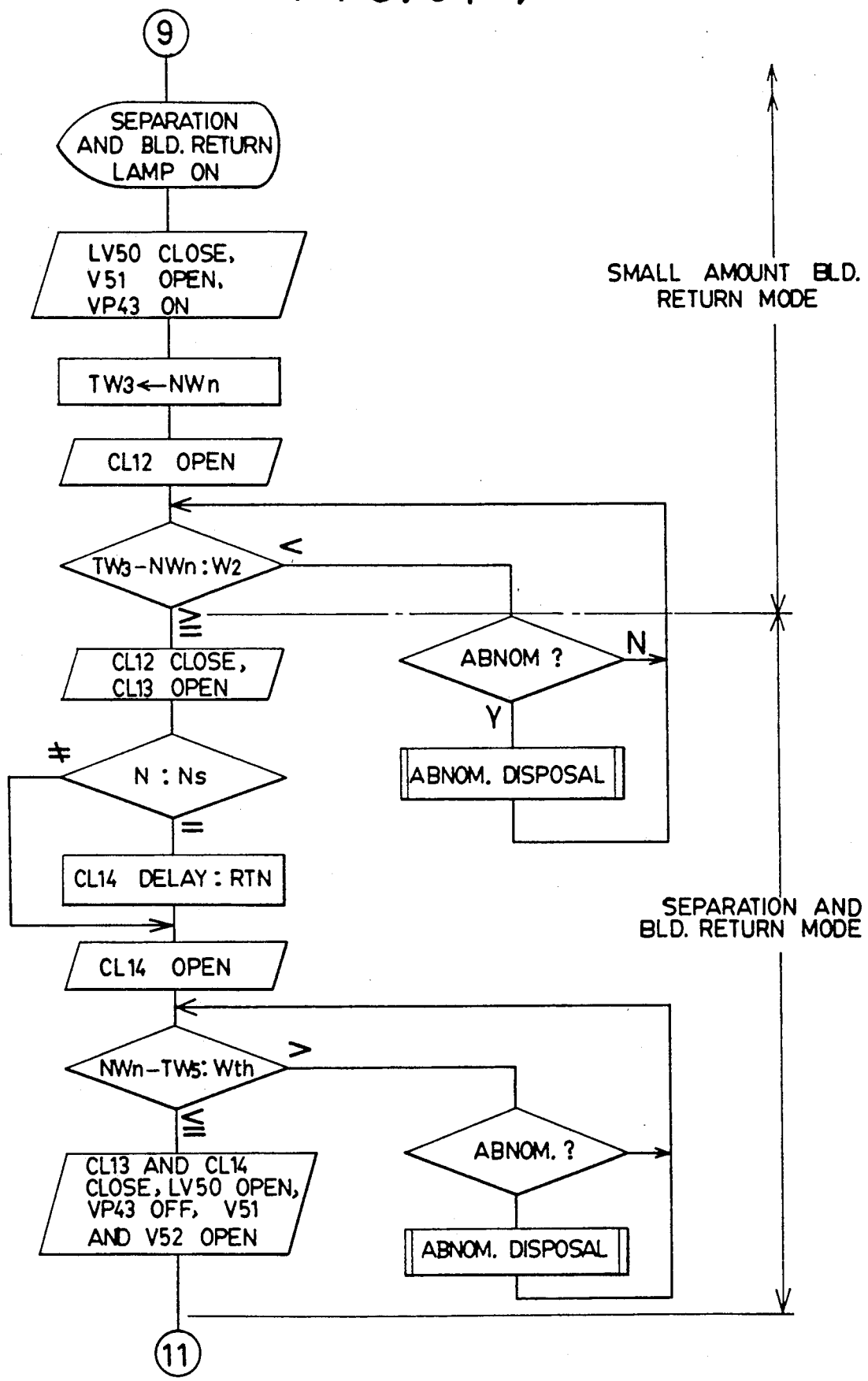
Figure 8F:
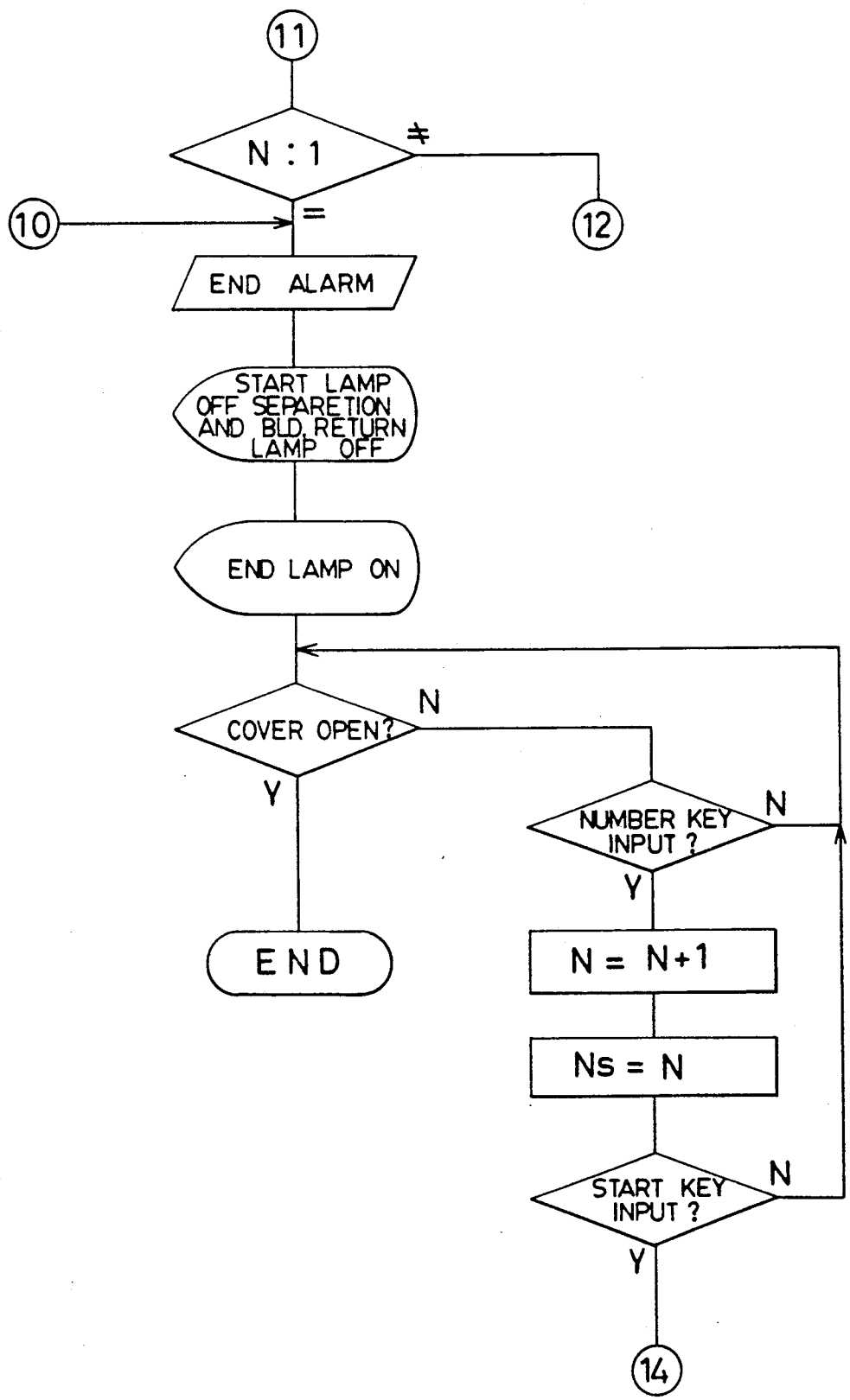
Figure 8G:
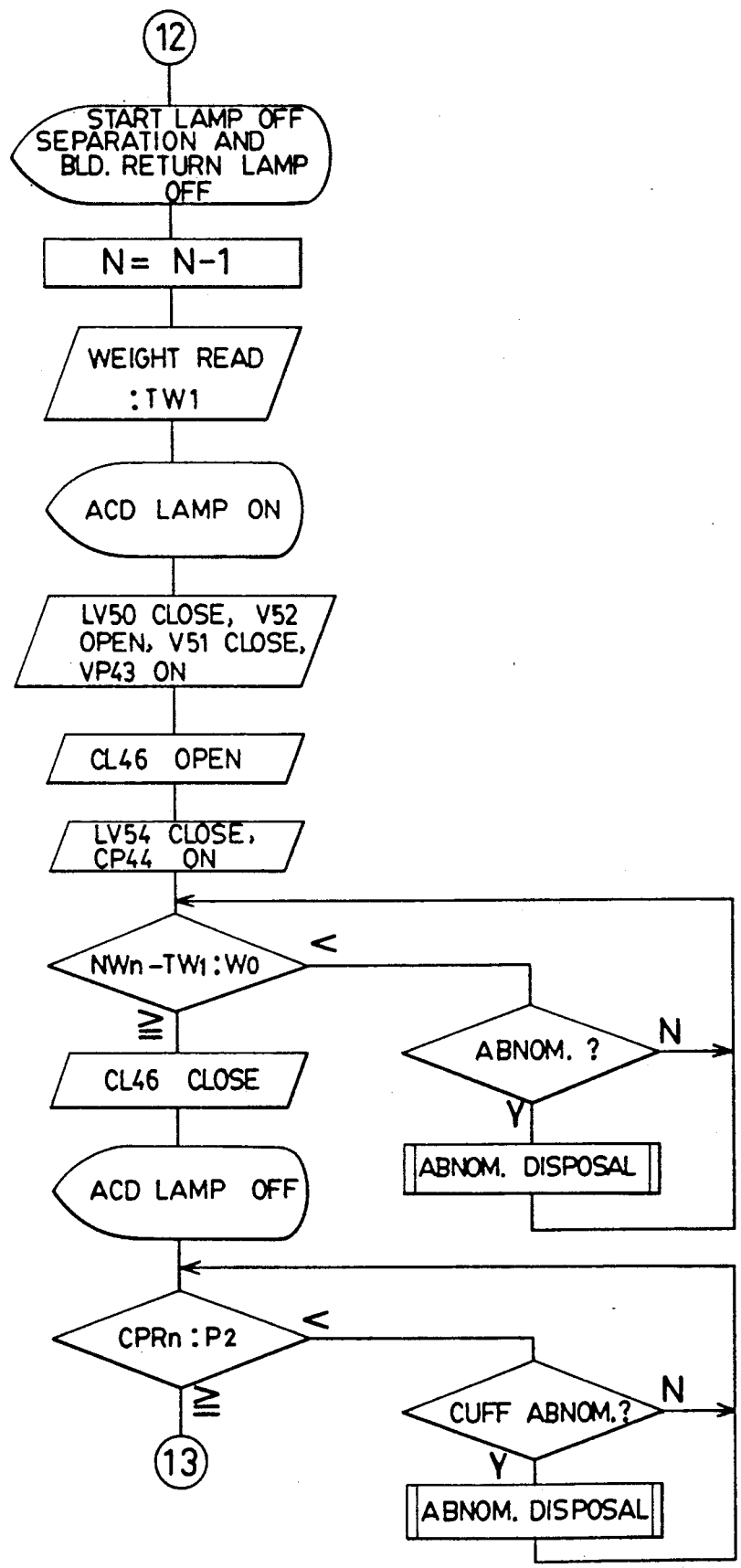

A concrete embodiment of the plasma collection apparatus having such a construction is shown in FIGS. 5 through 7. FIG. 5 is a perspective view of the embodiment of the plasma collection apparatus of the present invention to which the single-needle type plasma separation circuit is connected. FIG. 6 is a front elevation of the embodiment of the plasma collection apparatus of the present invention to which only the plasma separator is attached. FIG. 7 is a schematic cross sectional view taken along the center line of FIG. 6.

The plasma collection apparatus 40 of the present invention will be described more detailedly with reference to FIGS. 4 through 7.

The plasma collection apparatus 40 includes an inclined cover 83 in its upper wall. The cover 83 is provided with detecting means for detecting the opening and closing states of the cover. The detecting means comprises, for example, a magnet 86 disposed on the cover 83 and a Hall IC 87 as shown in FIG. 7. The blood collection container receiving portion 41 is defined as a closed space by the closed cover 83 as shown in FIG. 7. A blood collection container receiving table 98 in an inclined state is disposed in the blood collection container receiving portion 41.

Figure 11A:
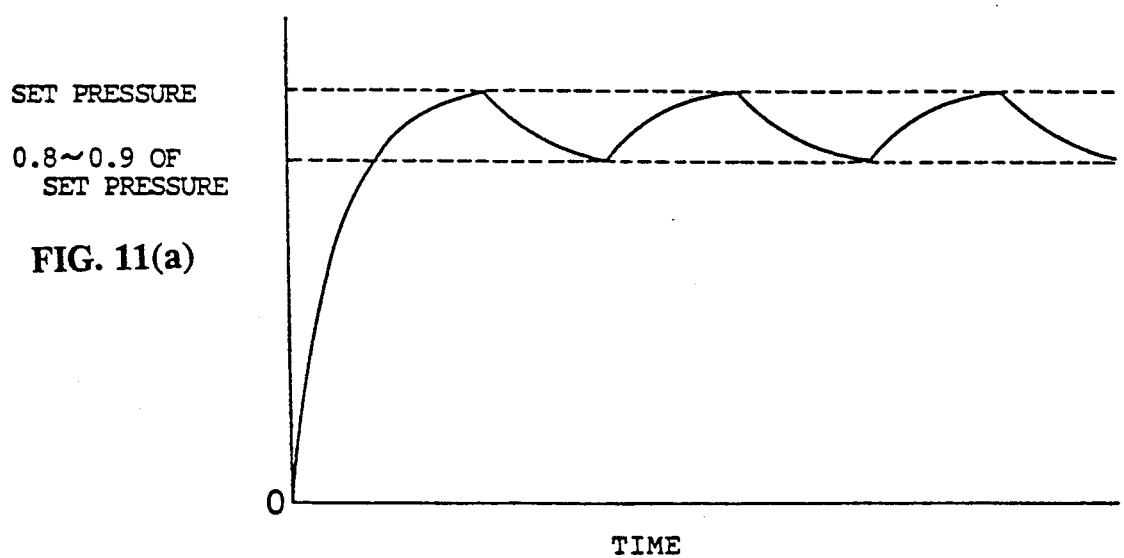
FIG. 11(a) is a graph representation for illustrating the set pressure maintain function by ON/OFF operations of a vacuum pump of the pressurizing and depressurizing means used in the plasma collection apparatus of the present invention.
Figure 11B:
FIG. 11(b) is a graph showing the ON/OFF operation of the vacuum pump.
Figure 13A:
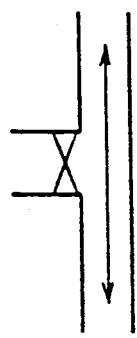
FIGS. 13(a) through 13(d) are schematic illustrations of one example of the pressurizing and depressurizing means used in the plasma collection apparatus of the present invention.
Figure 13B:
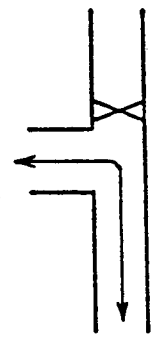
Figure 13C:
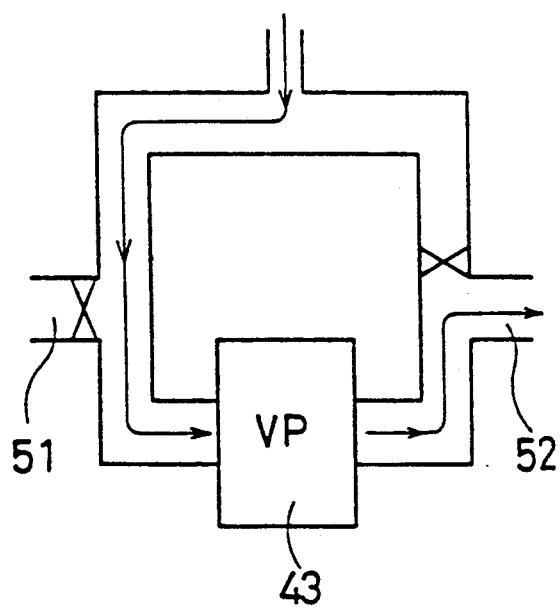
Figure 13D:
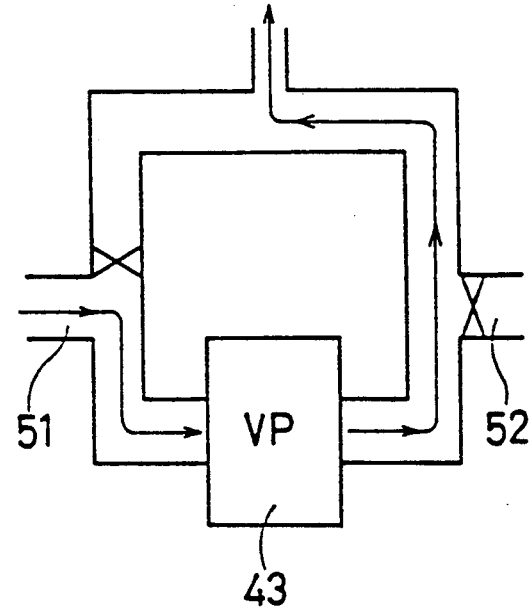
Figure 14:
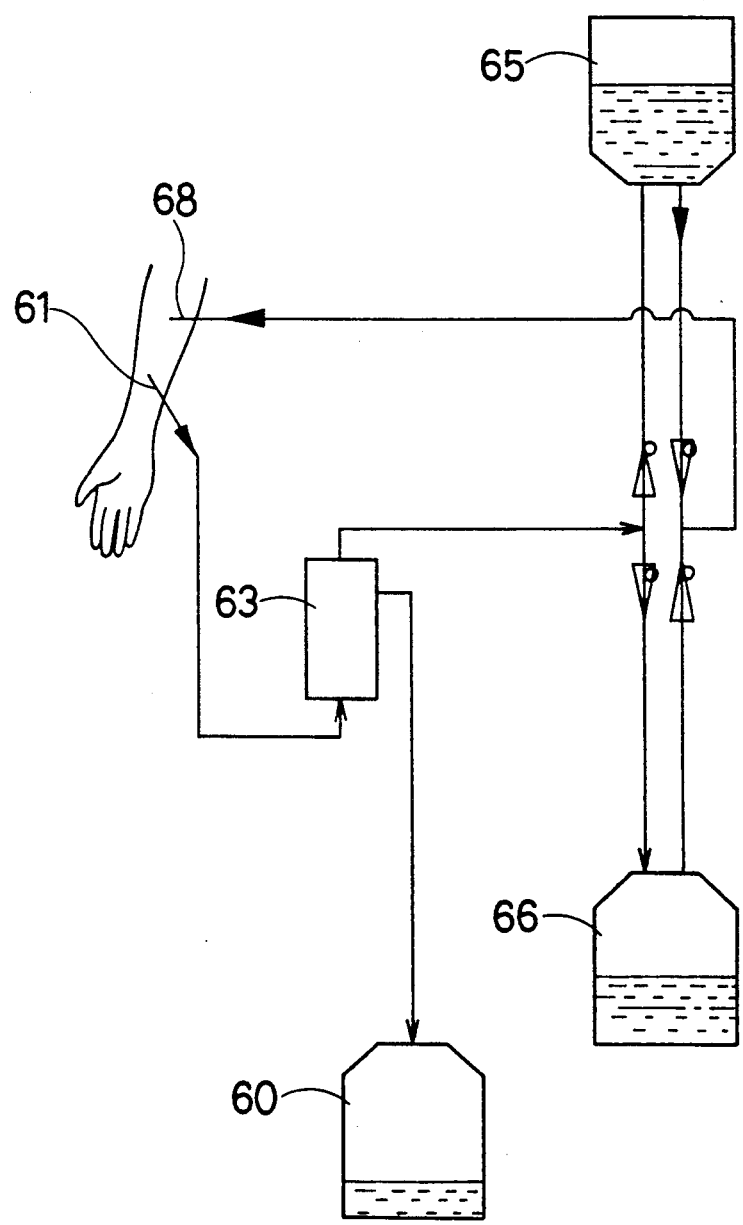
FIGS. 14 and 15 are schematic illustrations of prior art plasma separation apparatuses.
Figure 15:
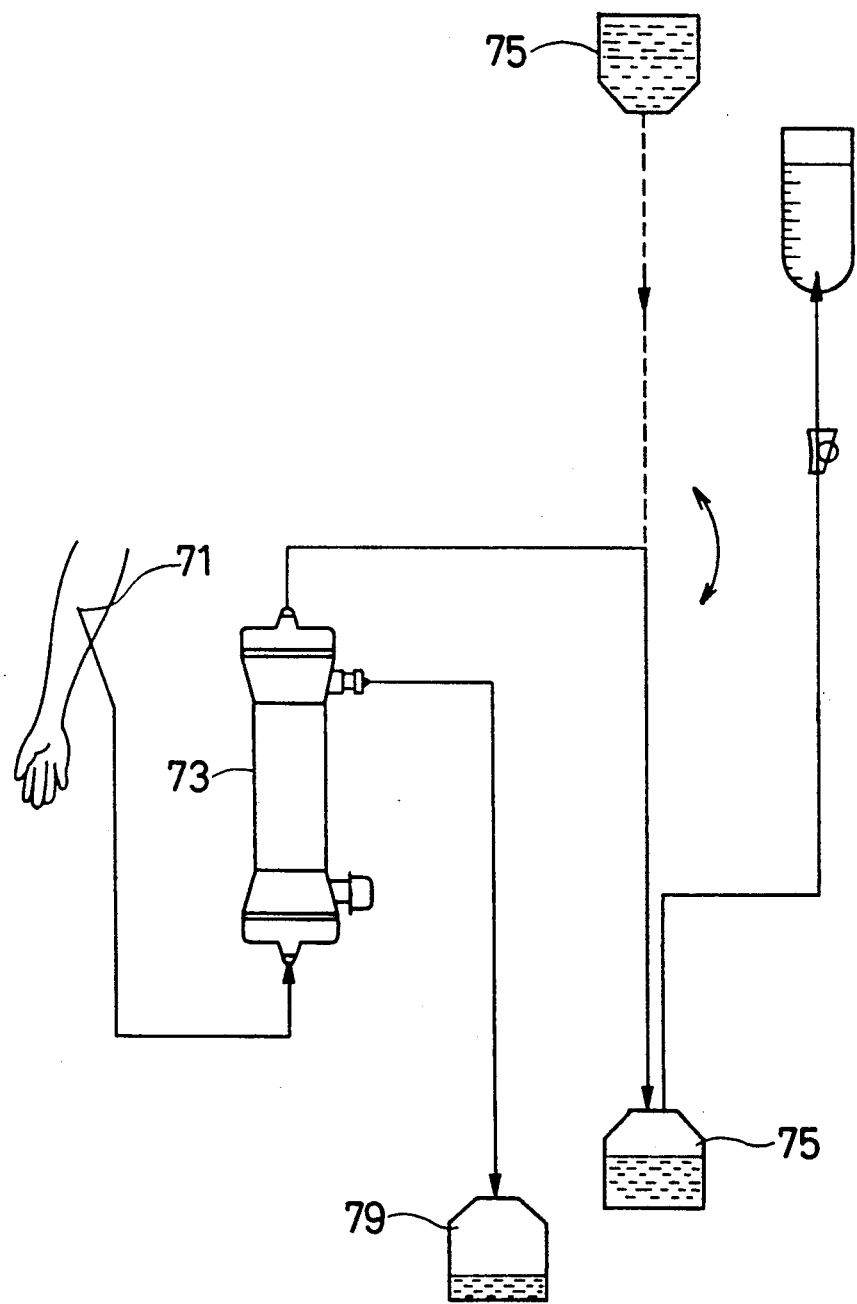

The blood collection container is mounted on the blood collection container receiving table 98 such that the tube connecting side of the blood collection container is lower than the other side, that is, the tube connecting side becomes the front side. The blood collection container receiving table 98 is pivotally supported in its front side and provided with swinging means comprising a swinging crank 90 and a motor 91 for driving up and down the swinging crank 90. The blood collection container receiving table 98 is supported in its initial state at an inclination angle of +20° with respect to the horizontal. The swinging means swings the blood collection container receiving table 98 with an amplitude of ±20° with respect to the horizontal. Pressurizing and depressurizing means is connected to the blood collection container receiving portion 41 to pressurize or depressurize the interior of the blood collection container receiving portion 41. The pressurizing and depressurizing means 58 comprises a feed and exhaust circuit 53, a vacuum pump 43 and two 3-port valves 51 and 52 as shown in FIG. 4a. The pressurizing and depressurizing means 58 can establish a depressurized state within the range of −100 to −200 mmHg by a step of 10 mmHg and a pressurized state within the range of +50 to +200 mmHg by a step of 10 mmHg. The set pressure can be input at a front panel 80 shown in FIGS. 5 and 6. The depressurized or pressurized state is maintained to substantially a constant pressure by ON/OFF operations of the vacuum pump 43 as shown in FIGS. 11(a) and 11(b). The depressurized and pressurized states are switched over by changing over the 3-port valves 51 and 52. The operation of the pressurizing and depressurizing means including the operations of the 3-port valves will be described with reference to FIGS. 13(a) to 13(d). Each of the 3-port valves 51 and 52 is in the pass-through mode in its ON state as shown in FIG. 13(a) and released to the atmosphere in its OFF state as shown in FIG. 13(b). Thus, when only the 3-port valve 51 is ON (the 3-port valve 52 is OFF) as shown in FIG. 13(c), air is exhausted by the operation of the vacuum pump 43 so that the interior of the blood collection container receiving portion 41 is depressurized. Contrarily, when only the 3-port valve 52 is ON (the 3-port valve 51 is OFF) as shown in FIG. 13d, air is sucked by the operation of the vacuum pump 43 so that the interior of the blood collection container receiving portion 41 is pressurized.

The blood collection container receiving portion 41 is provided with a pressure detecting means 55, for example, pressure sensor, for detecting the internal pressure of the blood collection container receiving portion 41 as shown in FIG. 4(a). Specifically, the pressure detecting means 55 is attached to be in fluid communication with the blood collection container receiving portion 41 through a tube. As the pressure detecting means, a carrier diffusion type semiconductor pressure sensor is suitably used. The blood collection container receiving portion 41 is further provided with a weight detecting means 57, for example, weight sensor as shown in FIG. 4(a). Specifically, the weight detecting means 57 is attached to the blood collection container receiving table 98. The weight detecting means is for detecting the weight of blood in the blood collection container. As the weight detecting means, a load cell is suitably used. The blood collection container receiving portion 41 is further provided with a blood leak sensor (not shown). The blood leak sensor is also attached to the blood collection container receiving table 98 so that the sensing surface of the sensor is exposed in the upper surface of the blood collection container receiving table 98. The blood leak sensor may be arranged as follows. For example, a spacer is mounted on the load cell constituting the weight detecting means and a printed board constituting the blood leak sensor is mounted thereon. The shut-off means 12, 13, 14 and 46 suitably comprise solenoid pinch valves which are closed in the ordinary state. A hanger 85 for the anticoagulant liquid container is disposed on the left side surface of the plasma collection apparatus 40 as shown in FIGS. 5 and 6. A plasma separator holder 84 constituting a plasma separator attachment portion is formed on the front surface of the plasma collection apparatus 40. The plasma separator holder 84 can rotate forwards arround an axis about 30 mm below the center of the plasma separator holder 84 to a position inclined by an angle of about 20° to receive the plasma separator. The plasma separator is detachably attached by a latch type magnet catch. A cuff pressure port 93 is formed in the front surface of the plasma collection apparatus 40. As shown in FIG. 4(a), a tube connected to the cuff 49 can be attached to the cuff pressure port 93. The cuff pressure port 93 is connected to a cuff pressurizing pump 44 disposed in the plasma collection apparatus 40. The cuff pressure port 93 is provided with a pressure sensor 56 for detecting the internal pressure of the port 93, and a leak valve 54. The cuff pressurizing pump 44 suitably comprises a small pump for sphygmomanometer. The pressure sensor 56 suitably comprises a carrier diffusion type semiconductor pressure sensor. The pressure applied to the cuff 49 from the cuff pressure port 93 is established within the range of +10 to +100 mmHg by a step of 10 mmHg. The set pressure can be input at the front panel 80 shown in FIGS. 5 and 6. The plasma collection apparatus is provided with a bubble detecting means 97 for detecting bubbles in the third blood transportation tube 8 as shown in FIG. 4(a). The bubble detecting means 97 suitably comprises a ultrasonic bubble sensor.

The operation of the single-needle type plasma separation apparatus of the present invention will be described with reference to FIG. 1

The shut-off means 11 and 12 are open, the shut-off means 13 and 14 and rleasing means 17 are closed, and the blood collection needle 21 is then stabbed into a vein of a donor. In this state, when the interior of the blood collection container receiving portion is depressurized to a predetermined pressure by the pressurizing and depressurizing means of the blood collection container receptacle 18, blood is collected in the blood collection container 5 from the blood collection needle 21 stabbed in the vein through the first blood transportation tubes 2a and 2b and blood chamber 3. The above-mentioned depressurized state is kept and the stirring function of the blood collection container receptacle 18 is effected so that blood is mixed with the anticoagulant liquid in the blood collection container. The stirring function of the blood collection container receptacle 18 may be started after a predetermined amount of blood is collected in the blood collection container 5 and the pressurizing and depressurizing means is stopped. After collecting a predetermined amount of blood, the shut-off means 11 is closed and the releasing means 17 is open so that blood remaining in the first blood transportation tube 2b flows into the blood collection container 5.

Subsequently, the blood return and plasma separation operation is carried out. The shut-off means 12 is closed, the shut-off means 11, 13 and 14 are open, and the releasing means 17 is closed. Then, the interior of the blood collection container receptacle 18 is pressurized to a predetermined pressure and the interior of the receiving portion of the plasma collection container receptacle 19 is depressurized to a predetermined pressure so that blood is transported from the blood collection container 5 to the plasma separator 7 through the second blood transportation tube 6. Plasma separated from blood in the plasma separator 7 is transported to the plasma collection container 10 through the plasma transportation tube 9. On the other hand, blood having a high Ht value (concentrated red blood cells) flowing out from the blood outlet 7b of the plasma separator 7 is returned to the vein through the third blood transportation tube 8, blood chamber 3, first blood transportation tube 2a and blood collection neddle 21.

Next, the operation of the plasma collection apparatus 40 of the present invention will be described with reference to FIGS. 4, 8(a) through 8(g), 9(a), 9(b) and 10.

The plasma collection apparatus 40 to which is connected the blood separation circuit comprising a blood collection needle 21; a blood collection container 5; a first blood transportation tube 2 connecting the blood collection needle 21 to the blood collection container 5; a blood separator 7; a second blood transportation tube 6 connecting the blood collection container 5 to a blood inlet of the blood separator 7; a third blood transportation tube 8 connecting a blood outlet of the blood separator 7 to the first blood transportation tube 2; a plasma collection container 10; a plasma transportation tube 9 connecting a plasma outlet of the plasma separator 7 to the plasma collection container 10; an anticoagulant liquid container 45; and an anticoagulant liquid transportation tube 48 connecting the anticoagulant liquid container 45 to the blood collection container 5, comprises a blood collection container receiving portion 41; pressurizing and depressurizing means 58 for pressurizing or depressurizing the interior of the blood collection container receiving portion 41; a plasma separator attachment portion for detachably attaching the plasma separator 7; first shut-off means 12 for closing the first blood transportation tube 2 of the blood separation circuit; second shut-off means 13 for closing the second blood transportation tube 6 thereof; third shut-off means 14 for closing the plasma transportation tube 9 thereof; and fourth shut-off means 46 for closing the anticoagulant liquid transportation tube 48.

The plasma collection apparatus 40 carries out an anticoagulant liquid injection step that the interior of the blood collection container receiving portion 41 is depressurized by the operation of the pressurizing and depressurizing means 58 so as to inject a predetermined amount of anticoagulant liquid into the blood collection container 5 from the anticoagulant liquid container 45; a blood collection step that the interior of the blood collection container receiving portion 41 is depressurized by the operation of the pressurizing and depressurizing means 58 after completion of the anticoagulant liquid injection step so as to collect a predetermined amount of blood into the blood collection container 5 from a donor; a small amount blood return step that the interior of the blood collection container receiving portion 41 is pressurized by the operation of the pressurizing and depressurizing means 58 after completion of the blood collection step so as to return the blood remaining in the first blood transportation tube 2 to the donor and flow the blood collected in the blood collection container 5 into the first blood transportation tube 2; and a separation and blood return step that the interior of the blood collection container receiving portion 41 is pressurized by the operation of the pressurizing and depressurizing means 58 after completion of the small amount blood return step so as to flow the blood collected in the blood collection container 5 into the plasma separator 7, collect plasma component into the plasma collection container 10 from the plasma outlet of the plasma separator 7, and return blood cell component to the donor from the blood cell outlet of the plasma separator 7.

The plasma collection apparatus 40 repeats the above-mentioned anticoagulant liquid injection step, blood collection step, small amount blood return step, and separation and blood return step in this order in a predetermined number of times. The execution of each step and the proceeding of the steps are substantially automated.

Here, an example that five times plasma collections are carried out using the blood collection container of 200 ml will be described with reference to FIGS. 8(a) through 8(g).

First, the power switch of the plasma collection apparatus 40 is turned on. The CPU is initialized and each part is automatically checked in its electrical abnormality. Subsequently, the set value of the blood collection amount (200 mml or 400 mml, here 200 mml), the set mode of the operation mode (only blood collection or apheresis, here apheresis), and the set number of times of blood collection (here 5 times) and default data of each set parameter are transferred to RAM. Further, if need, parameters such as blood collection pressure, blood return pressure, etc. are changed through parameter set switches arranged in the front surface of the plasma collection apparatus. After this, the cover 83 is opened and the shut-off means 12 (CL12), 13 (CL13), 14 (CL14) and 46 (CL46) are then opened. At this time, the leak valve 50 (LV50) of the pressurizing and depressurizing means 58 is released to the atmosphere as well as the pressurizing/depressurizing change-over valves 51 (V51) and 52 (V52) of the pressurizing and depressurizing means 58. The weight of the blood collection container receptacle 98 is then detected and the value detected is memorized as TW0. Next, if there is no error in setting of the blood collection container 5, the blood collection amount of 200 mml, the number of times of blood collection ($N_s$)=5, and the operation mode (apheresis) are input as a default data set. The single-needle type plasma separation circuit is then connected to the plasma collection apparatus 40, the tube connected to the cuff 49 is connected to the cuff pressure port 93 and the cuff 49 is attached to a donor. After completion of the above-mentioned setting, if the start switch on the front panel is turned on, then the flow chart advances to ③ in FIG. 8(b). In this operation, the weight of the blood collection container is detected (TW5). If the weight of the blood collection container is abnormal (TW0≧TW5), then an alarm is given because it has been detected that the blood collection container is not received in the blood collection container receiving portion, and the flow chart enters a mount disposal routin. Further, if there is a leak of blood or the cover is open, then an alarm is given. If no alarm is given, then a start lamp is lit, entering the anticoagulant liquid injection mode. In this mode, N=$N_s$(here N=5) is input and the detection of the pressure (BP) of the blood collection container receiving portion is started. Next, the operation mode is judged. Here, since the operation mode is "apheresis", the flow chart advances to ⑥. In this operation, an anticoagulant lamp (ACD lamp) is lit. The leak valve 50 (LV50) is then closed, the pressurizing/depres surizing change-over valve 52 (V52) is in the pass-through mode, and the shut-off means 46 (CL46) is opened. Further, the vacuum pump 43 (VP43) is operated to depressurize the interior of the blood collection container receiving portion 41. As a result, an anticoagulant liquid (for example, ACD liquid) is injected into the blood collection container 5 from the anticoagulant liquid container 45. If the operation mode is "only blood collection", then the flow chart advances to ⑤ in FIG. 8(c). The injection of the anticoagulant liquid is continued till the weight detecting means 57 detects the state that the weight that the weight of the blood collection container 5 before injection of the anticoagulant liquid ($NW_O$) is subtracted from the weight of the blood collection container 5 ($NW_N$) becomes more than the set anticoagulant liquid weight ($W_O$) ($NW_N - NW_O \geq W_O$). If this state is detected, then the vacuum pump 43 (VP43) is stopped, the shut-off means 46 (CL46) is closed, and the leak valve 50 (LV50) is opened, completing the injection of the anticoagulant liquid. While the state of $NW_N - NW_O \geq W_O$ is not detected in a predetermined time, it is always judged whether an abnormality occurs or not. If an abnormality occurs, then an abnormality disposal is carried out. Next, the cuff pressure (CPR) is detected, the leak valve 54 (LV54) is closed, and the cuff pressurizing pump 44 (CP44) is operated. If the cuff pressure becomes higher than a set value (P2) (CPR $\geq$ P2), then a standby alarm is given, the ACD lamp is put out, and the start lamp goes on and off. While the state of CPR $\geq$ P2 is not detected in a predetermined time, it is always judged whether the cuff pressure is abnormal or not. If it is abnormal, then an abnormality disposal is carried out and the flow chart advances to ⑦ in FIG. 8(c). Next, the puncture needle 21 is stabbed into a vein of a donor. After confirming that blood flows into the blood transportation tube through the puncture needle owing to the venous pressure of the donor, the start switch (start SW) disposed on the front panel 80 is turned on. By this operation, the blood collection mode is started. The leak valve 50 (LV50) is closed. The vacuum pump 43 is operated to depressurize the interior of the blood collection container receiving portion. The shut-off means 12 (CL12) is opened, the swing motor 42 is operated, and the blood collection lamp and start lamp are lit. The cuff pressure pump 44 is kept operated. The cuff pressure is maintained within a predetermined range by ON/OFF operations of the cuff pressure pump like the vacuum pump as described later. Blood flows into the blood collection container 5 by the operation of the above vacuum pump. The weight of the blood collection container 5 is successively detected by the weight detecting means 57. If the weight of the blood collection container 5 ($NW_N$) becomes more than a set weight ($W_1$ = blood collection set weight + anticoagulant liquid weight ($W_O$) ($NW_N \geq W_1$), then the shut-off valve 12 (CL12) is closed, the leak valve 50 (LV50) is released, the vacuum pump 43, swing motor 42 and cuff pressure pump 44 are stopped, and the valve 51 (V51) is also released to the atmosphere, completing the blood collection mode. While the state of $NW_N \geq W_1$ is not detected in a predetermined time, it is always judged whether an abnormality occurs or not. If an abnormality occurs, then an abnormality disposal is carried out. If additional swing data are set, the swing operation is done and the blood collection lamp is put out. Next, the operation mode (only blood collection or apheresis, here apheresis) is judged and the flow chart then advances to ⑨ in FIG. 8(e). If the operation mode is selected only blood collection, then the flow chart advances to ⑩ in FIG. 8(f). At this time, the small amount blood return mode is started and the separation and blood return lamp is lit. This small amount blood return mode is for the following purpose. At the end of the blood collection mode, blood to which no anticoagulant liquid is added remains in the first blood transportation tube 2. There is a possibility of formation of blood clogging in the first blood transportation tube 2. Therefore, in this small amount blood return mode, the blood remaining in the first blood transportation tube 2 is returned to the donor and blood to which an anticoagulant liquid has been added is fed into the first blood transportation tube 2, thereby preventing the formation of blood clogging in the first blood transportation tube 2. In the small amount blood return mode, the leak valve 50 (LV50) is closed, the valve 51 (V51) is released to the atmosphere, and the valve 52 is in the pass-through mode. The vacuum pump 43 is operated to pressurize the interior of the blood collection container receiving portion 41. The weight of the blood collection container 5 is memorized as TW3. The shut-off means 12 (CL12) is opened. The small amount blood return mode is continued till the weight that the weight of the blood collection container ($TW_N$) is substracted from the weight of the blood collection container before blood return (TW3) becomes more than a set blood return weight of anticoagulant liquid added blood ($W_2$) ($TW3 - TW_N \geq W_2$). If the above set value is reached, the small amount blood return mode is completed. While the state of $TW3 - TW_N \geq W_2$ is not detected in a predetermined time, it is always judged whether an abnormality occurs or not. If an abnormality occurs, then an abnormality disposal is carried out. The separation and blood return mode is started. The shut-off means 12 (CL12) is then closed and the shut-off means 13 (CL13) is opened. Next, the remaining number of times of blood collection is judged. If $N = N_s$, that is, it is judged that the blood collection is the first time, then the shut-off means 14 (CL14) is opened after a time. This is for the following reason. The plasma separator is first filled with a priming liquid (physiological saline). Thus, at the first time, only the priming liquid must be flown out by delaying the timing of open of the shut-off means 14 (CL14) by 10 to 20 seconds so that plasma may not be diluted by the priming liquid. In the separation and blood return mode, the shut-off means 13 (CL13) and 14 (CL14) are opened and the vacuum pump 43 (VP43) is kept operated. Thereby, blood flows into the plasma separator 7 from the blood collection container 5 and plasma component separated in the plasma separator 7 flows into the plasma collection container 10 through the plasma transportation tube 9. On the other hand, blood cell component is returned to the donor from the plasma separator 7 through the third and first blood transportation tubes 8 and 2. This operation is continued till the weight that the weight of the blood collection container 5 before the separation and blood return mode ($TW_5$) is substracted from the weight of the blood collection container 5 ($TW_N$) becomes less than a set weight ($W_{th}$) ($TW_N - TW_5 \leq W_{th}$). If the set weight is reached, then the shut-off means 13 (CL13) and 14 (CL14) are opened, the valves 51 (V51) and 52 (V52) are released to the atmosphere, and the vacuum pump 43 is stopped, completing the separation and blood return mode, then the flow chart advances to ⑪ in FIG. 8(f). While the state of $TW_N - TW_5 \leq W_{th}$ is not detected in a predetermined time, it is always judged whether an abnormality occurs or not. If an abnormality occurs, then an abnormality disposal is carried out. Next, it is judged whether the remaining number of times of blood collection is one or not (N:1). If the remaining number of times is not one, then the flow chart advaces to ⑫ in FIG. 8(g). In this operation, separation and blood return lamp and start lamp are put out. $N = N - 1$ is input to count down the remaining number of times. The weight of the blood collection container is memorized as TW1. The ACD lamp is lit again. The leak valve 50 (LV50) is closed, the valve 51 (V51) is in the pass-through mode, the valve 52

(V52) is released to the atmosphere, and the vacuum pump 43 (VP43) is operated. The shut-off means 14 (CL14) is opened, the leak valve 54 (LV54) is closed, and the cuff pressure pump 44 (CP44) is operated. An anticoagulant liquid (for example, ACD liquid) is injected into the blood collection container from the anticoagulant liquid container 45 till the weight that TW1 is subtracted from the weight of the blood collection container 5 ($NW_N$) becomes more than the set anticoagulant liquid weight ($W_O$) ($NW_N - TW1 \geq W_O$). If the above set value is reached, then the shut-off means 46 (CL46) is closed, the vacuum pump 43 is stopped, and the ACD lamp is put out. While the state of $NW_N - TW1 \geq W_O$ is not detected in a predetermined time, it is always judged whether an abnormality occurs or not. If an abnormality occurs, then an abnormality disposal is carried out. Next, if the cuff pressure becomes higher than a predetermined value ($CPR_N \geq P2$), then the flow chart advances to ⑬ in FIG. 8(d) to start the blood collection mode again. While the state of $CPR_N \geq P2$ is not detected in a predetermined time, it is always judged whether an abnormality occurs or not. If an abnormality occurs, then an abnormality disposal is carried out.

If it is judged that the remaining number of times of blood collection is one (N=1), and end alarm is given, the start lamp and the separation and blood return lamp are put out, and an end lamp is lit. The puncture needle 21 is then withdrawn from the donor. By opening the cover of the plasma collection apparatus 40, all of the shut-off means 12, 13, 14 and 46 are opened and the end lamp is put out. The blood collection container is put out from the blood collection container receiving portion and the plasma separator is detached from the plasma separator attachment portion, completing the plasma collection operation. Otherwise, not opening the cover but inputting the number of times of blood collection (N) through the number key and operating the start key again, the flow chart advances to ⑭ in FIG. 8(b) to start the anticoagulant liquid injection mode again.

In this flow chart, if an abnormality occurs in the detection of the weight of the blood collection container or cuff pressure, an abnormality disposal is carried out by detecting the occurrence of the abnormality.

Figure 9A:
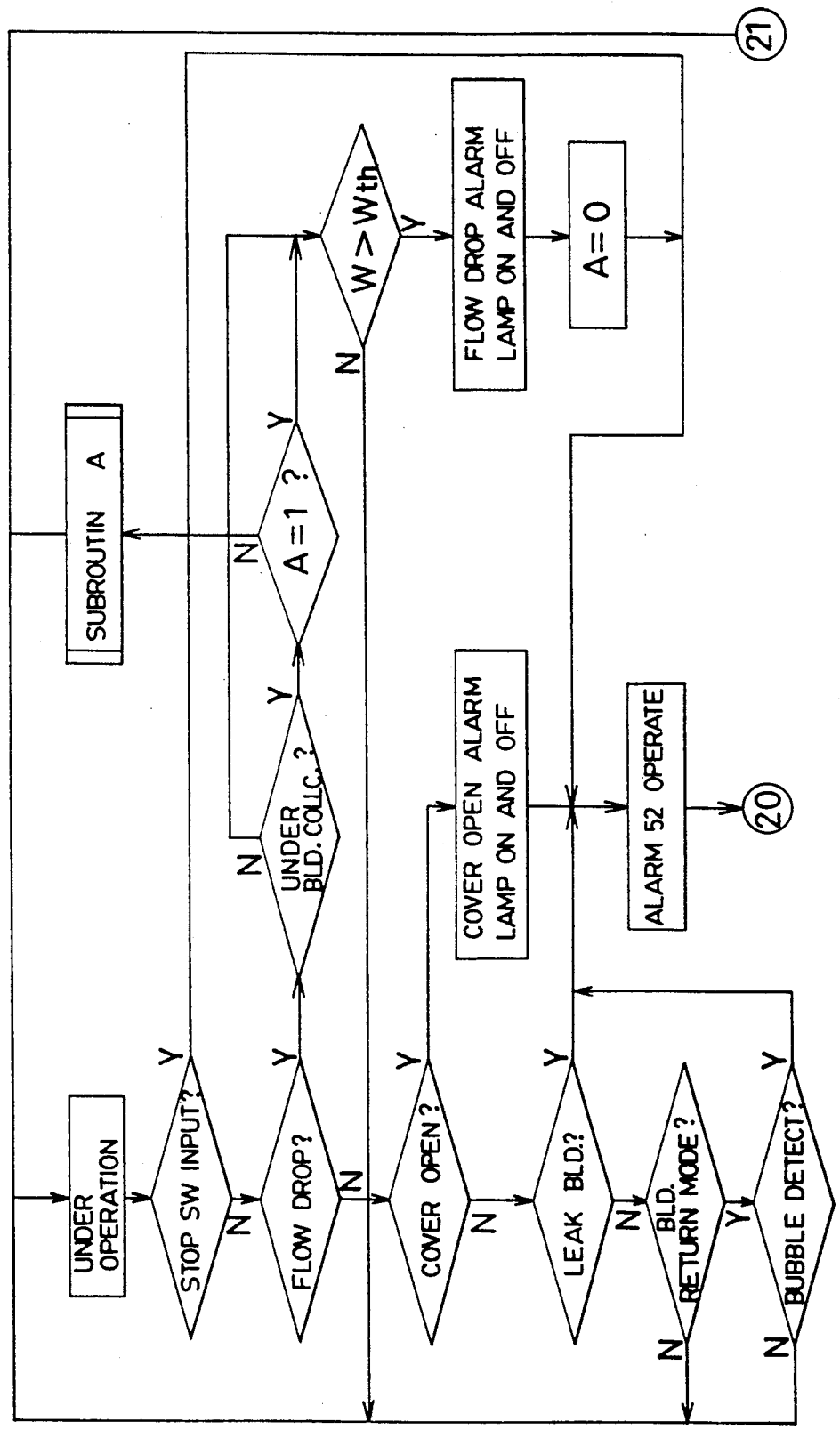
FIGS. 9(a), 9(b) and 10 are flow charts for illustrating the operation of the embodiment of the plasma collection apparatus of the present invention.
Figure 9B:
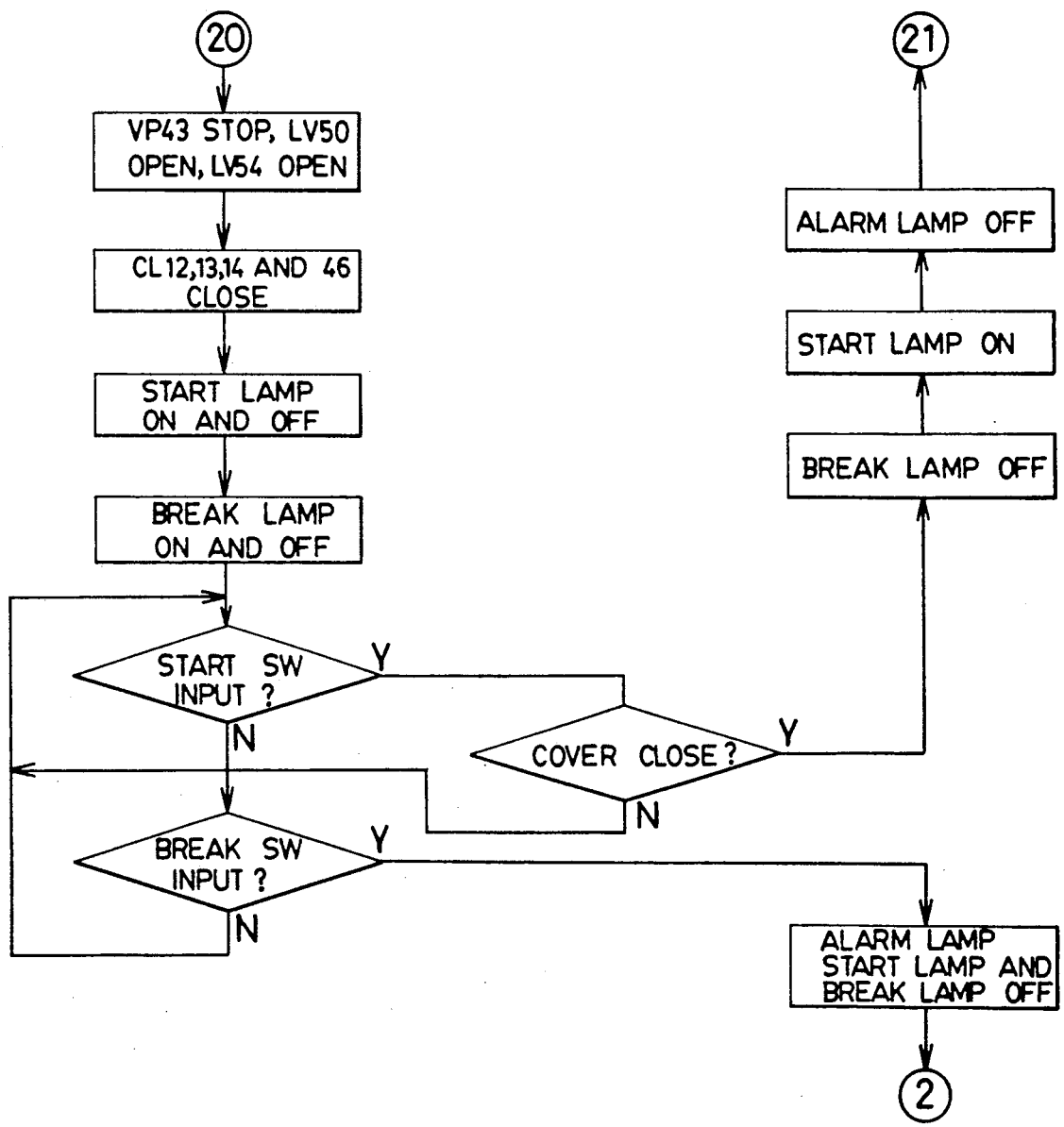
Figure 10:
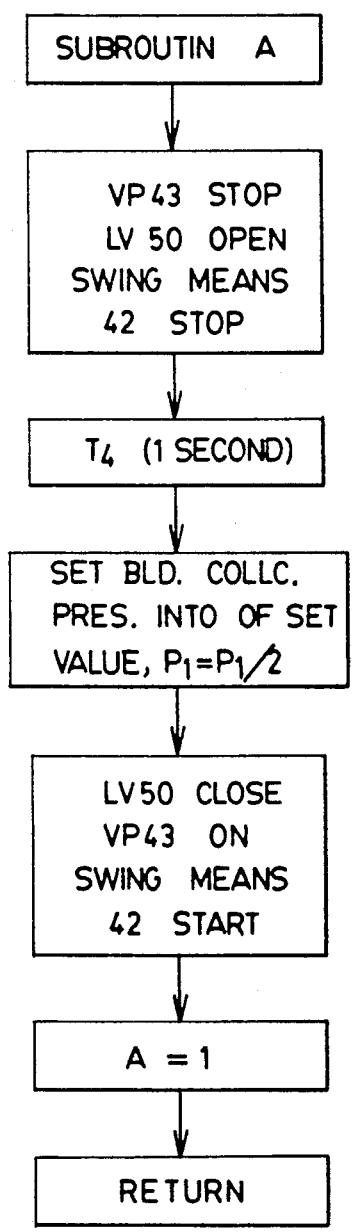

Next, a warning flow of the plasma collection apparatus 40 of the present invention will be described with reference to FIGS. 9(a), 9(b) and 10. Referring to FIGS. 9(a) and 9(b), during operation of the plasma collection apparatus 40, it is always judged in order whether the stop switch is operated or not, whether there is a drop of the flow rate of collected blood or not, whether the cover is open or not, there is a leak of blood or not, and there is a bubble or not in separation and blood return mode as shown by the left side route of FIG. 9(a). If the judgement is YES in each step, the flow chart enters the warning flow. In this time, if the drop of the flow rate of collected blood is detected, then it is judged whether it is in the blood collection mode or not. If it is in the blood collection mode, then it is judged whether A=1 (if A=1, it means another drop of the flow rate of collected blood). If A≠1, the flow chart enters a subroutin A shown in FIG. 10. In the plasma collection apparatus 40, the internal pressure of the blood collection container receiving portion 41 is maintained by ON/OFF operations of the vacuum pump within a range between the upper limit of a set pressure and the lower limit of 0.8-0.9 of the set pressure as shown in FIG. 11. The weight detecting means disposed in the blood collection container receiving portion 41 detects the weight of the blood collection container by a period of the swing motion by the swinging means 42 of the blood collection container receiving portion 41. A detected value is compared with the value detected 15 seconds before to detect a drop of the flow rate of collected blood. If the drop of the flow rate of collected blood is detected, then the flow chart enters the subroutin A shown in FIG. 10 as described above. In this subroutin A, as shown in FIGS. 10 and 12, the vacuum pump 43 (VP43) and swinging means 42 are stopped and the leak valve 50 is opened. This state is kept for one second ($T_4$). Then, the pressure for blood collection is automatically set at ½ of the set pressure ($P_1$), that is, $P_1/2$. The vacuum pump 43 (VP43) and swinging means 42 are then operated and the leak valve 50 (LV50) is closed. Next, A=1 is automatically input and blood collection is started again. If another drop of the flow rate of collected blood occurs, A=1 is judged as shown in the flow chart of FIG. 9(a). It is then judged whether or not the value that the predetermined weight ($TW_5$) is subtracted from the weight of the blood collection container 5 ($NW_N$) is more than the set weight ($W_{th}$) ($NW_N - TW_5 > W_{th}$). If this judgment is YES (if NO, it corresponds to the condition of FIG. 8(e)), a flow drop alarm lamp goes on and off, A=0 is automatically input, and an alarm 82 is operated, then the flow chart advances to ⑳ in FIG. 9(b). The vacuum pump 43 (VP43) and swinging means 42 are then stopped and the leak valves 50 (LV50) and 54 (LV54) are released as shown in FIGS. 9(b) and 12(a). Next, all of the shut-off means (CL12, 13, 14 and 46) are closed and the start lamp and an break lamp go on and off. Next, it is judged whether the start switch is ON or OFF and whether the break switch is ON or OFF. If it is detected that the start switch is on and the cover is closed, the break lamp is put out, the start lamp goes on, the alarm lamp is put out and the flow chart advances to ㉑ in FIG. 9(b). If it is detected that the break switch is ON, the alarm lamp, start lamp and break lamp are put out and the flow chart advances to ② of the flow chart of FIG. 8(a) to break off the plasma collection operation.

Next, examples of the present invention will be described.

EXAMPLE 1

ACD added bovine blood of 446 ml regulated to Ht 40% was contained by the blood collection container. The blood collection container containing the above blood was received by the blood collection container receiving portion of the blood collection container receptacle. The internal pressure of the blood collection container receiving portion of the blood collection container receptacle was set at 60 mmHg. The plasma collection container was received in the plasma collection container receptacle and the internal pressure thereof was set at −30 mmHg. The plasma collection container receptacle was Hemoquick (registered trade mark of TERUMO KABUSHIKI KAISHA). The circuit construction was as shown in FIG. 1, where the shut-off means 11, 13 and 14 were opened and the shut-off means 12 and releasing means 17 were closed. The treatment time of the blood of 446 ml was 16 minutes and 35 seconds and plasma of 196 ml could be collected.

EXAMPLE 2

An experiment was carried out similarly to that of Example 1 except a head h between the plasma outlet of the plasma separator and the plasma collection container 10 was 47 cm instead of using the plasma collection container receptacle as shown in FIG. 2. Substantially the similar results to those of Example 1 were obtained.

EXAMPLE 3

The plasma collection apparatus as described above with reference to FIGS. 4a through 9 was prepared. The single-needle type plasma collection circuit had the circuit construction shown in FIG. 4a. The puncture needle was 16G and the plasma separator was a flat membrane lamination type. ACD added bovine blood of 4 l regulated to Ht 40% was contained by the container. The puncture needle was inserted in the container to carry out the plasma collection experiment. The blood collection container receiving portion of the plasma collection apparatus was depressurized to −180 mmHg upon blood collection and pressurized to +155 mmHg upon blood return. The period of the swing motion was 3 seconds. The amount of blood collected in one time was 228 ml. The number of times of blood collection was five. The container containing the above bovine blood was agitated with a rotor during plasma collection operation. The results of the plasma collection are given in the following table 1.

TABLE 1

| Number | Time of blood collection | Time of blood return | Amount of plasma collection (g) |
|---|---|---|---|
| 1 | 1′ 37″ | 2′ 14″ | 81.8 |
| 2 | 1′ 41″ | 2′ 29″ | 89.2 |
| 3 | 1′ 42″ | 2′ 25″ | 86.0 |
| 4 | 1′ 42″ | 2′ 36″ | 84.2 |
| 5 | 1′ 43″ | 2′ 40″ | 82.0 |
| Total | 22′ 10″ | | 423.2 |

The single-needle type plasma separation apparatus of the present invention comprises a blood collection needle; a blood collection container; a first blood transportation tube connecting the blood collection needle to the blood collection container; a blood separator; a second blood transportation tube connecting the blood collection container to a blood inlet of the blood separator; a third blood transportation tube connecting a blood outlet of the blood separator to the first blood transportation tube; a plasma collection container; a plasma transportation tube connecting a plasma outlet of the plasma separator to the plasma collection container; and a blood collection container receptacle including a receiving portion for the blood collection container and capable of pressurizing and depressurizing the interior of the receiving portion. Particularly, the single-needle type plasma separation apparatus of the present invention is provided with the blood collection container receptacle including the receiving portion for the blood collection container and capable of pressurizing and depressurizing the interior of the receiving portion. Thereby, it is possible to carry out the collection of blood into the blood collection container, the transportation of the collected blood to the plasma separator, and the return of the concentrated red blood cells from the plasma separator. Therefore, the present invention affords the advantages that the circuit construction is simple, the whole size of the apparatus is small, the apparatus can be used even in a narrow car for blood donation because there is no necessity for ensuring a head for circulating blood through a plasma separator, parts to be handled can be gathered, improving the operability, and plasma can easily be collected. Furthermore, the blood transportation tubes connecting the components to one another can be shortened, the volume for priming of the plasma separation apparatus can be made small, and an automation of the operation becomes possible. Besides, because the second blood transportation tube is not in fluid communication with the first blood transportation tube in the apparatus of the present invention, blood never flows into the second blood transportation tube upon blood collection. Thus, the removal of blood from the second blood transportation tube is not required.

If a blood chamber is disposed in the middle of the first blood transportation tube and the blood chamber is provided with a communicating tube including an air filter and a releasing means to the atmosphere, blood remaining in the first blood transportation tube can be transported to the blood collection tube, utilizing blood effectively.

In the plasma separation apparatus of the present invention, blood is first collected in the blood collection container and plasma is then separated in the blood return line. Therefore, by disposing an anticoagulant liquid in the blood collection container in advance, it becomes possible to eliminate an anticoagulant liquid injection line.

Alternatively, if the blood collection container is provided with an anticoagulant liquid transportation tube and an anticoagulant liquid container connected to the anticoagulant liquid transportation tube, plural times of blood collection and plasma separation can be carried out with a single blood collection container.

The plasma collection apparatus of the present invention to which is connected a blood separation circuit comprising a blood collection needle; a blood collection container; a first blood transportation tube connecting the blood collection needle to the blood collection container; a blood separator; a second blood transportation tube connecting the blood collection container to a blood inlet of the blood separator; a third blood transportation tube connecting a blood outlet of the blood separator to the first blood transportation tube; a plasma collection container; and a plasma transportation tube connecting a plasma outlet of the plasma separator to the plasma collection container, comprises a blood collection container receiving portion; pressurizing and depressurizing means for pressurizing or depressurizing the interior of the blood collection container receiving portion; a plasma separator attachment portion for detachably attaching the plasma separator; first shut-off means for closing the first blood transportation tube of the blood separation circuit; second shut-off means for closing the second blood transportation tube thereof; and third shut-off means for closing the plasma transportation tube thereof. Therefore, plasma can be easily collected by using the above plasma separation circuit.

Further, if the plasma collection apparatus includes a controller for controlling the pressurizing and depressurizing means, and first, second and third shut-off means on the basis of output of the weight detecting means, the plasma collection operation can be automated, facilitating plasma collection.

We claim:

1. A single-needle type plasma separation apparatus comprising: a blood collection needle; a blood collection container; a first blood transportation tube connecting said blood collection needle to said blood collection container; a plasma separator; a second blood transportation tube connecting said blood collection container to a blood inlet of said plasma separator; a third blood transportation tube connecting a blood outlet of said plasma separator to said first blood transportation tube; a plasma collection container; a plasma transportation tube connecting a plasma outlet of said plasma separator to said plasma collection container; a receptacle accommodating said blood collection container in its interior, a pressurizing means for selectively pressurizing and depressurizing the interior of said receptacle; and control means for actuating said pressurizing means to depressurize the interior of said receptacle to transport blood into said blood collection container through said first blood transportation tube, and for pressurizing the interior of said receptacle to transport blood into said plasma separator from said blood collection container.

2. A single-needle type plasma separation apparatus according to claim 1, wherein a blood chamber is disposed in the middle of said first blood transportation tube, said blood chamber being provided with a communicating tube having an air filter and a releasing means to the atmosphere.

3. A single-needle type plasma separation apparatus according to claim 1, wherein said receptacle is provided with stirring means for stirring blood collected in said blood collection container.

4. A single-needle plasma separation apparatus according to claim 1, wherein said apparatus further comprises a receptacle accommodating said plasma collection container in its interior, and depressurizing means for depressurizing the interior of said receptacle.

5. A single-needle type plasma separation apparatus according to claim 1, wherein an anticoagulant liquid is contained in said blood collection container.

6. A plasma collection apparatus to which is connected a blood separation circuit comprising: a blood collection needle; a blood collection container; a first blood transportation tube connecting said blood collection needle to said blood collection container; a plasma separator; a second blood transportation tube connecting said blood collection container to a blood inlet of said blood separator; a third blood transportation tube connecting a blood outlet of said plasma separator to said first blood transportation tube; a plasma collection container; and a plasma transportation tube connecting a plasma outlet of said plasma separator to said plasma collection container; a receptacle accommodating said blood collection container in its interior; pressurizing means for pressurizing or depressurizing the interior of said receptacle; first shut-off means for closing said first blood transportation tube of said blood separation circuit; second shut-off means for closing said second or third blood transportation tube thereof; and third shut-off means for closing said plasma transportation tube thereof; and control means for actuating said pressurizing means to depressurize the interior of said receptacle to transport blood into said blood collection container through said first blood transportation tube, and for pressurizing the interior of said receptacle to transport blood into said plasma separator from said blood collection container.

7. A plasma collection apparatus according to claim 6, wherein said plasma collection apparatus further comprises pressure detecting means for detecting the pressure of the interior of said receptacle.

8. A plasma collection apparatus according to claim 6, wherein said plasma collection apparatus further comprises weight detecting means for detecting the weight of said receptacle container received by said blood collection.

9. A plasma collection apparatus according to claim 8, wherein said control means actuates said first, second and third shut-off means on the basis of the output of said weight detecting means.

10. A plasma collection apparatus according to claim 6, wherein said plasma collection apparatus further comprises swinging means for agitating said blood collection container received by said receptacle.

11. A plasma collection apparatus according to claim 6, wherein said single-needle type plasma separation circuit further comprises an anticoagulant liquid container and an anticoagulant liquid transportation tube connecting said anticoagulant liquid container to said blood collection container, and said plasma collection apparatus further comprises fourth shut-off means for closing said anticoagulant liquid transportation tube.

12. A plasma collection apparatus according to claim 11, wherein said control means actuates said fourth shut-off means.

13. A plasma collection apparatus according to claim 6, wherein said plasma collection apparatus further comprises pressurizing means for pressurizing a cuff attached to a donor.

14. A plasma collection apparatus according to claim 13, wherein said plasma collection apparatus further comprises cuff pressure detecting means.

15. A plasma collection apparatus according to claim 6, wherein said single-needle type plasma separation circuit further comprises an anticoagulant liquid container and an anticoagulant liquid transportation tube connecting said anticoagulant liquid container to said blood collection container, and said plasma collection apparatus further comprises pressure detecting means for detecting the pressure of the interior of said receptacle, weight detecting means for detecting the weight of said blood collection container accommodated in said receptacle, swinging means for agitating said blood collection container accommodated in said receptacle, fourth shut-off means for closing said anticoagulant liquid transportation tube, pressurizing means for pressurizing a cuff attached to a donor, and cuff pressure detecting means, and said control means actuates said pressurizing means and said first, second, third and fourth, shut-off means on the basis of the output of said weight detecting means.

16. A plasma collection apparatus according to claim 15, wherein said control means actuates said swinging means and said pressurizing means for cuff on the basis of the output of said weight detecting means.

17. A plasma collection apparatus to which is connected a blood separation circuit comprising: a blood collection needle; a blood collection container containing an anticoagulant liquid; a first blood transportation tube connecting said blood collection needle to said blood collection container; a plasma separator; a second blood transportation tube connecting said blood collection container to a blood inlet of said plasma separator; a third blood transportation tube connecting a blood outlet of said plasma separator to said first blood transportation tube; a plasma collection container; and a plasma transportation tube connecting a plasma outlet of said plasma separator to said plasma collection container; a receptacle accommodating said blood collection container in its interior; pressurizing means for pressurizing or depressurizing the interior of said receptacle; first shut-off means for closing said first blood transportation tube of said blood separation circuit; second shut-off means for closing said second blood transportation tube thereof; and third shut-off means for closing said plasma transportation tube thereof; control means for (a) carrying out a blood collection step by actuating said pressurizing means to depressurize the interior of said receptacle so as to collect a predetermined amount of blood into said blood collection container from a donor, (b) carrying out a small amount blood return step by actuating said pressurizing means to pressurize the interior of said receptacle after completion of said blood collection step so as to return blood remaining in said first blood transportation tube to said donor and flow the blood collected in said blood collection container, and to which said anticoagulant liquid has been added, into said first blood transportation tube, and (c) a carrying out a separation and blood return step by actuating said pressurizing means to pressurize the interior of said receptacle after completion of said small amount blood return step so as to flow the blood collected in said blood collection container into said plasma separate, collect a plasma component into said plasma collection container from said plasma outlet of said plasma separator, and return a red blood cell component to said donor from the blood cell outlet of said plasma separator.

18. A plasma collection apparatus according to claim 17, further comprising weight detecting means for detecting the weight of said blood collection container received by said receptacle, and wherein said control means actuates said pressurizing means, and said first, second and third shut-off means on the basis of the output of said weight detecting means.

19. A plasma collection apparatus to which is connected a blood separation circuit comprising: a blood collection needle; a blood collection container; a first blood transportation tube connecting said blood collection needle to said blood collection container; a plasma separator; a second blood transportation tube connecting said blood collection container to a blood inlet of said plasma separator; a third blood transportation tube connecting a blood outlet of said plasma separator to said first blood transportation tube; a plasma collection container; a plasma transportation tube connecting a plasma outlet of said plasma separator to said plasma collection container; an anticoagulant liquid container; and an anticoagulant liquid transportation tube connecting said anticoagulant liquid container to said blood collection container; a receptacle accommodating said blood collection container in its interior; pressurizing means for pressurizing or depressurizing the interior of said receptacle; first shut-off means for closing said first blood transportation tube of said blood separation circuit; second shut-off means for closing said second blood transportation tube; third shut-off means for closing said plasma transportation tube; and fourth shut-off means for closing said anticoagulant liquid transportation tube; control means for (a) carrying out an anticoagulant liquid injection step by actuating said pressurizing means to depressurize the receptacle so as to inject a predetermined amount of anticoagulant liquid into said blood collection container from said anticoagulant liquid container, (b) carrying out a blood collection step by actuating said pressurizing means to depressurize said receptacle after completion of said anticoagulant liquid injection step so as to collect a predetermined amount of blood into said blood collection container from a donor (c) carrying out a small amount blood return step by actuating said pressurizing means to pressurize said receptacle after completion of said blood collection step so as to return blood remaining in said first blood transportation tube to said donor and flow the blood collected in said blood collection container, and to which said anticoagulant liquid has been added, into said first blood transportation tube, and (d) carrying out a separation and blood return step by actuating said pressurizing means to pressurize the receptacle after completion of said small amount blood return step so as to flow the blood collected in said blood collection container into said plasma separator, collect a plasma component into said plasma collection container from said plasma outlet of said plasma separator, and return a red blood cell component to said donor from the blood cell outlet of said plasma separator.

20. A plasma collection apparatus according to claim 19, wherein said control means repeats said anticoagulant liquid injection step, said blood collection step, said small amount blood return step, and said separation and blood return step in this order in a predetermined number of times.

21. A plasma collection apparatus according to claim 20, further comprising weight detecting means for detecting the weight of said blood collection container received by said receptacle, and wherein said control means actuates said pressurizing means, and said first, second, third and fourth shut-off means on the basis of the output of said weight detecting means.

* * * * *